United States Patent
Wang et al.

(10) Patent No.: US 12,134,797 B2
(45) Date of Patent: Nov. 5, 2024

(54) HYBRIDIZATION CAPTURE METHODS AND COMPOSITIONS

(71) Applicant: INTEGRATED DNA TECHNOLOGIES, INC., Coralville, IA (US)

(72) Inventors: Alexandra Hui Wang, Mountain View, CA (US); Katharine Dilger, Foster City, CA (US); Rachael Cunningham, Los Altos, CA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 21 days.

(21) Appl. No.: 17/212,247

(22) Filed: Mar. 25, 2021

(65) Prior Publication Data
US 2022/0090177 A1   Mar. 24, 2022

Related U.S. Application Data

(60) Provisional application No. 63/000,140, filed on Mar. 26, 2020.

(51) Int. Cl.
*C12Q 1/6832* (2018.01)

(52) U.S. Cl.
CPC .................................. *C12Q 1/6832* (2013.01)

(58) Field of Classification Search
CPC ............ C12Q 2537/159; C12Q 1/6806; C12Q 1/6832; C12Q 1/6834; C12Q 2527/107; C12Q 2527/125; C12Q 2563/131; C12Q 2563/143; C12Q 2563/149
See application file for complete search history.

(56) References Cited

U.S. PATENT DOCUMENTS

| | | |
|---|---|---|
| 2007/0087370 A1 | 4/2007 | Curry |
| 2008/0242555 A1 | 10/2008 | Shen et al. |
| 2014/0031240 A1* | 1/2014 | Behlke .................. C12Q 1/6876 536/24.3 |
| 2017/0096706 A1 | 4/2017 | Behlke et al. |

FOREIGN PATENT DOCUMENTS

WO   2017181670 A1   10/2017

OTHER PUBLICATIONS

International Search Report and Written Opinion for Application No. PCT/US2021/024069 dated Jun. 25, 2021 (14 pages).
Gruenwedel et al., "Salt effects on the denaturation of DNA", Biopolymers, vol. 7, No. 4, 1969, pp. 557-570.
Gruenwedel et al., "The effects of aqueous neutral-salt solutions on the melting temperatures of deoxyribonucleic acids", Biopolymers, vol. 10, No. 1, 1971, pp. 47-68.
Vaduevamurthy et al., "Betaine Structure and the presence of hydroxyl groups alters the effects on DNA melting temperatures", Biopolymers, vol. 91, No. 1, 2008, pp. 85-94.
Yin and Zhao, "Kinetics and Dynamics of DNA Hybridization", Accounts of Chemical Research, vol. 44, No. 11, 2011, pp. 1172-1181.
Wang et al., "Direct and sensitive miRNA profiling from low-input total RNA", RNA, vol. 13, No. 1, 2007, pp. 151-159.
Melchior et al., "Alteration of the Relative Stability of dA.dT and dG.dC Base Pairs in DNA", Proceedings of National Academy of Sciences, vol. 70, No. 2, 1973, pp. 298-302.
Canadian Patent Office Action for Application No. 3,167,021, dated Jul. 28, 2023 (4 pages).
European Patent Office Action for Application No. 21719425.7, dated Dec. 19, 2024 (7 pages).

* cited by examiner

*Primary Examiner* — Young J Kim
(74) *Attorney, Agent, or Firm* — Michael Best & Friedrich LLP

(57) ABSTRACT

Described herein are methods and compositions for improved hybridization capture for enriching for target nucleic acid sequences from a population of nucleic acids. In one aspect, the methods and compositions are useful for Next Generation Sequencing (NGS) applications. The methods and compositions include combining in solution capture probes and target nucleic acid and permitting hybridization of the target nucleic acid to the capture probes under conditions to promote efficient hybridization. Following hybridization, the probe/target complex is immobilized to a capture material while simultaneously incubating at an optimum hybridization temperature. The incubation denatures unwanted nucleic acids from the capture probes further enriching for target nucleic acid.

21 Claims, 15 Drawing Sheets

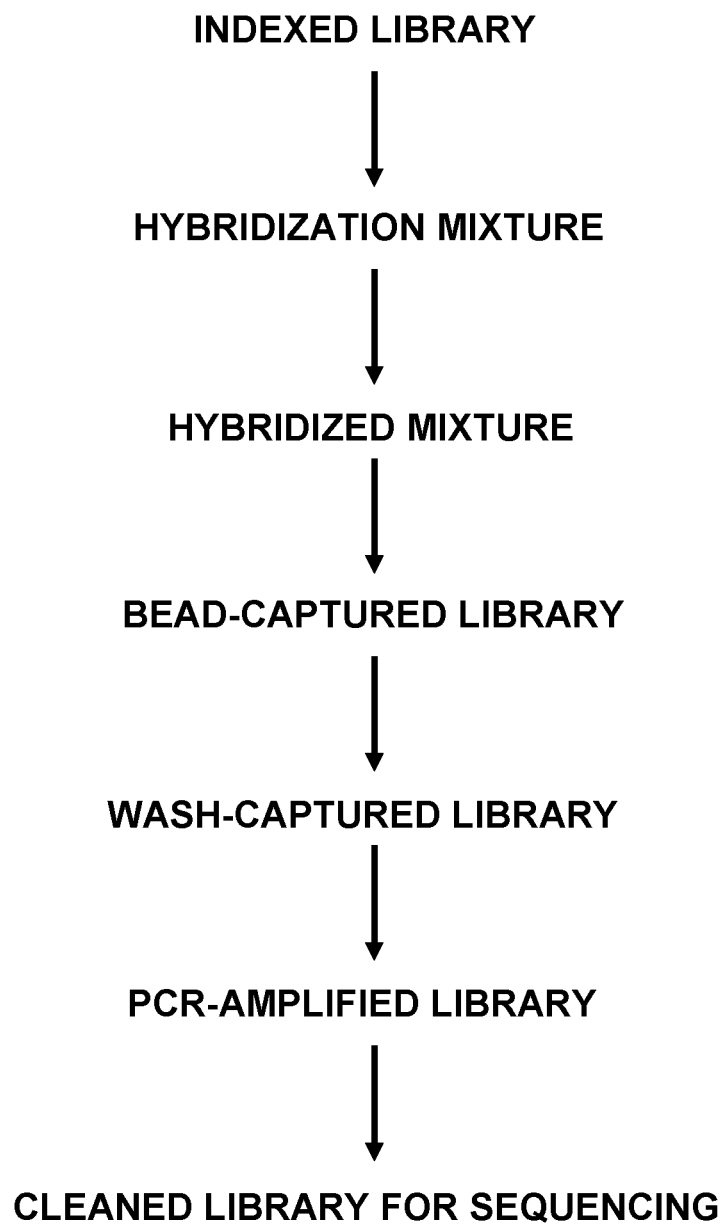

FIG. 3

STANDARD HYB-CAPTURE WORKFLOW

HYBRIDIZATION: Contact biotinylated-probe panel with NGS library

Probe hybridizes with high specificity

- Long incubation (hours to days)
- Hybridization kinetic traps
- Ideal results at associate-dissociation equlibrium (>> 24 hr)

↓

CAPTURE: Immobilize probe on streptavidin beads

Immobilize probe on bead with minimal non-specific binding

- Long binding at high temperatures with mixing (45-min 65 °C, mixing)
- Stringent conditions to minimize non-specific hybridization

↓

WASH: Remove non-targeted material

Non-targeted material on probes and bead surfaces are removed

- High temperature wash step followed by multiple lower temperature washes

↓

PCR: Amplify target on beads

FIG. 4

HYB-CAPTURE-MELT WORKFLOW

HYBRIDIZATION: Contact biotinylated-probe panel with NGS library

Specificity is secondary to yield
- Goal is improved yields
- Kinetic approach; equilibrium not required

CAPTURE: Immobilize probe on streptavidin beads

All probes, with and without bound targets are immobilized
- Rapid lower temperature capture to ensure integrity of streptavidin
- No mixing

MELT: Immobilized probe on streptavidin beads

Achieves specificity
Dissociates non-specific targets
- Rapid high-temperature incubation
- Stringency can be tuned based on temperature and conditions

WASH: Remove non-targeted material

Non-targeted material on probes and bead surfaces are removed
- No high-temperature wash
- Rapid and simple low temperature washes

PCR: Amplify target on beads

HYBRIDIZATION CAPTURE METHODS AND COMPOSITIONS

CROSS REFERENCE TO RELATED APPLICATIONS

This application claims priority to U.S. Provisional Patent Application No. 63/000,140, filed on Mar. 26, 2020, the contents of which are incorporated by reference herein in their entirety.

TECHNICAL FIELD

Described herein are methods and compositions for improved hybridization capture for enriching for target nucleic acid sequences from a population of nucleic acids. In one aspect, the methods and compositions are useful for Next Generation Sequencing (NGS) applications.

BACKGROUND

In DNA and RNA analysis, it is often more efficient to interrogate a selected population of target sequences within a complex sample, such as a sample from a genome, multiple genomes, cfDNA, ctDNA, RNA, or FFPE samples to detect multiple changes. The selected sequences are targeted for isolation ("target capture") for downstream workflows, such as amplification, point-of-care detection, sequencing, or chemical/biological propagation.

Two approaches to target capture are Hybridization Target Capture (hyb-capture) or Multiplex PCR (Amplicon Enrichment).

Multiplex PCR technologies are fast, sensitive, and usually provide an easy and efficient workflow that is often user friendly. However, the number of target sequences that can be simultaneously interrogated (captured) is limited to at most a few thousand of PCR-primer pairs. Additionally, uninterrupted representation of continuous long sequences (several kilobases), capture uniformity, and quantitative measurements are challenging. Some of the multiplex-PCR challenges are generally addressed by existing hybridization capture technologies.

Other methods, such as Molecular Inversion Probes (MIPs) or Padlock Probes, encounter similar changes of amplicon enrichment-based methods.

There are various methods of commercial hybridization-capture (hyb-capture) methods. For hyb-capture, nucleic acids may include, but are not limited to, dsDNA, dsRNA, or hybrid DNA-RNA complexes. Capture of any nucleic acid species relies on a similar approach of capturing a subset of target sequences from a complex mixture based on hybridization under conditions predicted by double stranded nucleic acid melting temperature ($T_m$). Hyb-capture methods follow the general workflow:

(A) A complex sample, such as a library of genomic DNA (target nucleic acid), is incubated with a pool of thousands or hundreds of thousands of targeting probe (or "bait") sequence in a specifically formulated hyb-capture solution.

(B) The targeting probes are hybridized to a target sequence in the form of amplifiable template. The hybridized complex is then frequently, captured by another substrate. The capture often entails additional incubation, often in combination with mixing.

(C) The capture material of Step B is washed vigorously in multiple steps to eliminate off-target nucleic acid and the resulting enriched capture material is prepared for sequencing. If the capture material of Step B is extended to form an amplifiable template suitable for sequencing, there is no need for the wash steps of Step C. However, extension of target materials suffers from reduced plexity.

Typical hybridization capture methods contact probes with targets under conditions deemed "specific" for expected probe-target melting temperatures ($T_m$). $T_m$ is usually determined empirically by heating (melting) a duplex nucleic acid under specific conditions. Such direct experimental observation is then either applied directly or used to calculate/predict the $T_m$ of the hybridization capture condition. Notably, $T_m$ does not account for the complicated kinetics and probability in the association and formation of a duplex in samples with biological complexity. The probe and target need to first associate by chance nucleation. For productive nucleation events, the probe-target pair needs to "sample" each other. See Yin and Zhao, *Acc. Chem. Res.* 44(11): 1172-1181 (2011). The duration of such associations and "sampling" is dependent on the hybridization conditions and the degree of complementarity. Such association/sample events occur continuously and iteratively until the system reaches its lowest energy state (thermodynamic equilibrium). Notably, an off-target association with adequate level of complementarity can tie up the probe-target pair for an extended duration and prevent each from hybridizing with the fully complementary target nucleic acid. Such mis-paired double stranded nucleic acid can endure the entire hybridization-capture process. Prolonged incubation at high temperature maximizes preferred target/probe hybridization reducing off-target pairs. Hybridization-capture is typically performed just below or at the expected duplex $T_m$ to minimize formation of off-target hybridizations; off-target duplex is expected to have lesser base-pairing thus lower $T_m$ and duration than the intended target/probe complex. Current approaches overlook the fact that such energy differential is reflected by the molecular population only when the system is at its thermodynamic equilibrium, which can take a long time to achieve. Empirical data with oligonucleotide systems on microarray showed such equilibrium is approached (not reached) with constant and highly vigorous mixing after 40 hours at high temperature. Wang et al., *RNA* 13(1): 151-159 (2007). Hybridization of longer and more complex probe-target mixes likely take longer to approach equilibrium, even if similar temperature stringency and rigorous mixing can be achieved on non-closed platform. As a result, hybridization-capture requires long incubation to approach uniformity and yield, even with ideal probe design and hybridization conditions.

While hybridization-capture can achieve very high complexity (multiple hundreds of thousands of probe sequences simultaneously in a single capture reaction) and can provide continuous and quantitative coverage of longer stretches of the genome, the workflow is long and arduous. A typical workflow involves many time-sensitive, hands-on steps performed by an experienced operator in order to achieve reproducible and consistent results. Further, coverage uniformity and specificity are challenges, which are usually compensated by probe design, hybridization-solution formulation optimization, hybridization duration, and stringency of post hybridization-capture wash steps. Assays still generally suffer from under or over sampling of GC or AT-rich regions.

What are needed are methods and compositions to overcome the existing challenges of current technologies and reduce the complexity of workflows, decrease the hybridization-capture time, increase the capture complex target regions, and improve the specific and uniform capture of target sequences or regions.

SUMMARY

Described herein are methods and compositions for improved hybridization capture for enriching for target nucleic acid sequences from a population of nucleic acids. The method includes: combining in solution a population of nucleic acids and a complementary probe set; permitting the complementary probe set to hybridize or bind to the target nucleic acid; selectively immobilizing the probe/target nucleic acid complex; exposing the selectively immobilized probe/target nucleic acid complex to a temperature below the aggregate $T_m$ to melt unwanted non-target material; and washing the complex to remove the unbound non-target material, thereby enriching for target nucleic acid.

One embodiment described herein pertains to the ability to reduce the hybridization time of the hybridization capture. One aspect described herein reduces the complexity of hybridization capture workflows. Another aspect described herein increases the capture specificity of complex target regions. Another aspect described herein improves the specific capture of target nucleic acid sequences or regions while minimizing sequence bias.

Another embodiment described herein provides for improved hybridization capture compositions. Another aspect described herein provides for improved hybridization capture buffers.

Another embodiment described herein is a method for hybridization capture. The hybridization capture method is a Hyb-Capture-Melt workflow. In a first step a probe panel is contacted with a nucleic acid sample under conditions to promote hybridization. Optionally, the probe panel may contain a capture moiety, for example, but not limited to biotinylation. The biotinylated probes are complementary to target nucleic acids or nucleic acids to be enriched for. In the first step the goal is to increase the hybridization capture yield. Specificity of the nucleic acid capture is secondary to yield. In a second step the biotinylated probes are immobilized to streptavidin beads. Probes with and without hybridized targets are immobilized. In a third step a melt is performed to dissociate all non-specific hybridization interactions. Without being bound to a single theory it is also expected that after the melt is performed re-hybridization of captured probes with target sequence occurs, further improving both yield and specificity. In a fourth step a wash step is performed to further remove un-hybridized and weakly hybridized non-targeted nucleic acids.

Another embodiment described herein is improved compositions for hybridization capture. In one aspect, hybridization capture buffers are provided that improve the hybridization capture efficiency. In another aspect, $T_m$ modifying reagents may be added. In another aspect, additives that decrease $T_m$ dependence on double stranded target GC base content may be added to improve capture.

Another embodiment described herein is a method for hybridization capture. In one step, a hybridization at low stringency is provided. In another step, capture (immobilization) is performed at a temperature sufficient to promote immobilization. In another step, a melt is performed at an elevated temperature to reduce off-target hybridization. In another step, a wash is performed to reduce off-target hybridization and optionally this wash step may be in the absence of a hot-wash.

One embodiment described herein is a method for enrichment of a population of nucleic acid target sequences in a sample comprising: (a) providing a sample of nucleic acid molecules comprising a plurality of target nucleic acid sequences and a plurality of off-target nucleic acid sequences; (b) hybridizing the sample to a panel of nucleic acid probes that are complementary to the plurality of target nucleic acid sequences under hybridization conditions to generate a probe/target complex; (c) selectively immobilizing the probe/target complex to form an immobilized probe/target complex; (d) heating the immobilized probe/target complex to a temperature at or below the aggregate $T_m$ of the probe/target complex for a period of time sufficient to disassociate the off-target nucleic acid sequences; and (e) washing the immobilized probe/target complex to remove non-hybridized nucleic acid sequences and off-target nucleic acid sequences from the hybridized plurality of target nucleic acid sequences, thereby enriching for the plurality of target nucleic acid sequences in the sample. In one aspect, the panel of nucleic acid probes that are complementary to the plurality of target nucleic acid sequences further comprises a capture moiety. In another aspect, the capture moiety is biotin. In another aspect, the hybridization conditions comprise a hybridization buffer comprising one or more of: (a) salts selected from one or more of monovalent, divalent, sodium, ammonium, cesium, or manganese, chlorides, citrates, sulfates, perchlorates, isothiocyanates, or guanidinium; (b) chelating agents selected from one or more of ethylenediaminetetraacetic acid (EDTA), ethylene glycol-bis(p-aminoethyl ether)-N,N,N',N'-tetraacetic acid (EGTA), or (1,2-bis(o-aminophenoxy)ethane-N,N,N',N'-tetraacetic acid (BAPTA); (c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris (hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N, N'-bis(2-ethanesulfonic acid) (PIPES); 2-(N-morpholino) ethanesulfonic acid (MES); or dimethylarsenic acid (Cacodylate); (d) detergents selected from one or more of sodium dodecylsulfate (SDS), polysorbate 20 (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA). In another aspect, the hybridization buffer contains formamide. In another aspect, the hybridization buffer does not contain formamide.

In one embodiment, the hybridization conditions comprise an incubation time ranging from 10 minutes to 48 hours. In one aspect, the hybridization conditions comprise an incubation time ranging from 2 hours to overnight. In another aspect, equivalent specificity and equivalent yield are achieved with a 2-hour incubation time as compared to an overnight incubation time. In another aspect, the hybridization conditions comprise an incubation temperature ranging from about 55° C. to about 75° C. In another aspect, the hybridization conditions comprise an incubation temperature ranging from about 60° C. to about 70° C. In another aspect, the hybridization conditions comprise an incubation time of 2 hours and an incubation temperature of about 65° C.

In another embodiment, the probe/target complex is selectively immobilized using streptavidin beads. In one aspect, the probe/target complex is selectively immobilized under conditions comprising an incubation time ranging from about 10 minutes to about 48 hours. In another aspect, the probe/target complex is selectively immobilized under conditions comprising an incubation temperature ranging from about 20° C. to about 40° C. In another aspect, the probe/target complex is selectively immobilized under conditions comprising an incubation time of about 30 minutes and an incubation temperature of room temperature. In another aspect, the heating of the immobilized probe/target complex comprises a melt buffer comprising one or more of: (a) salts selected from one or more of monovalent, divalent, sodium, ammonium, cesium, or manganese, chlorides, citrates, sulfates, perchlorates, isothiocyanates, or guanidinium; (b) chelating agents selected from one or more of ethylenediaminetetraacetic acid (EDTA), ethylene glycol-bis(β-aminoethyl ether)-N,N,N',N'-tetraacetic acid (EGTA), or (1,2-bis(o-aminophenoxy)ethane-N,N,N',N'-tetraacetic acid (BAPTA); (c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate); (d) detergents selected from one or more of sodium dodecylsulfate (SDS), polysorbate 20 (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylarsine hydrochloride, ethylene carbonate, dextran sulfate, or bovine serum albumin (BSA).

In another embodiment, the heating of the immobilized probe/target complex comprises an incubation time ranging from about 5 minutes to about 1 hour. In one aspect, the heating of the immobilized probe/target complex comprises an incubation temperature ranging from about 50° C. to about 70° C. In another aspect, the heating of the immobilized probe/target complex comprises an incubation time of about 20 minutes and an incubation temperature of about 55° C. In another aspect, the washing of the immobilized probe/target complex comprises two distinct wash buffers, wherein each wash buffer independently comprises one or more of: (a) salts selected from one or more of monovalent, divalent, sodium, ammonium, cesium, or manganese, chlorides, citrates, sulfates, perchlorates, isothiocyanates, or guanidinium; (b) chelating agents selected from one or more of ethylenediaminetetraacetic acid (EDTA), ethylene glycol-bis(p-aminoethyl ether)-N,N,N',N'-tetraacetic acid (EGTA), or (1,2-bis(o-aminophenoxy)ethane-N,N,N',N'-tetraacetic acid (BAPTA); (c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate); (d) detergents selected from one or more of sodium dodecylsulfate (SDS), polysorbate 20 (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

In another embodiment, the washing of the immobilized probe/target complex comprises an incubation time of about 5 minutes to about 15 minutes and an incubation temperature of about 60° C. In one aspect, the method improves specificity and enhances yield as compared to a conventional method. In another aspect, the conventional method does not comprise a step of heating prior to washing. In another aspect, the method improves on-target percentage as compared to a conventional method. In another aspect, the conventional method does not comprise a step of heating prior to washing. In another aspect, the method reduces handling time and throughput time as compared to a conventional method. In another aspect, the conventional method does not comprise a step of heating prior to washing. In another aspect, the method is suitable for automation and reduces complexity as compared to a conventional method. In another aspect, the conventional method does not comprise a step of heating prior to washing.

Another embodiment described herein is a plurality of target nucleic acid sequences isolated using the methods described herein.

Another embodiment described herein is a means for isolating a plurality of target nucleic acid sequences comprising any of the means, methods, steps, or compositions described herein.

Another embodiment described herein is the use of the methods described herein to isolate a plurality of target nucleic acid sequences.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows a flowchart of a standard workflow for preparation of a library for sequencing using hybridization capture.

FIG. 3 shows a schematic of a workflow for preparation of a library for sequencing using a standard hybridization capture workflow and describes the parameters at each step.

FIG. 4 shows a flowchart of the simplified "melt' hybridization capture workflow that simplifies the steps, reduces hands-on time and turnaround time, and increases specificity, enhances yields, and reduces size bias.

FIG. 7A shows on-target percentage and FIG. 7B shows flanked on-target percentage. The targeting panel used contained 18,815 targeting probes and was hybridized with 250 ng capture input NA12878 gDNA library. The Melt-Simple Bind at 30 min (e.g. Short Hyb 30) performed similarly to the standard overnight hybridization. The improvements of the Melt-Simple bind approach are most clearly observed in the 30-minute hybridizations.

FIG. 8A shows on-target percentage and mean with and without melting and FIG. 8B shows flanked on-target percentage and mean with and without melting. The targeting panel used here contains 18,815 targeting probes and was hybridized with 250 ng capture input NA12878 gDNA library. The melting process has higher specificity than the process without melting.

DETAILED DESCRIPTION

Figure 1:
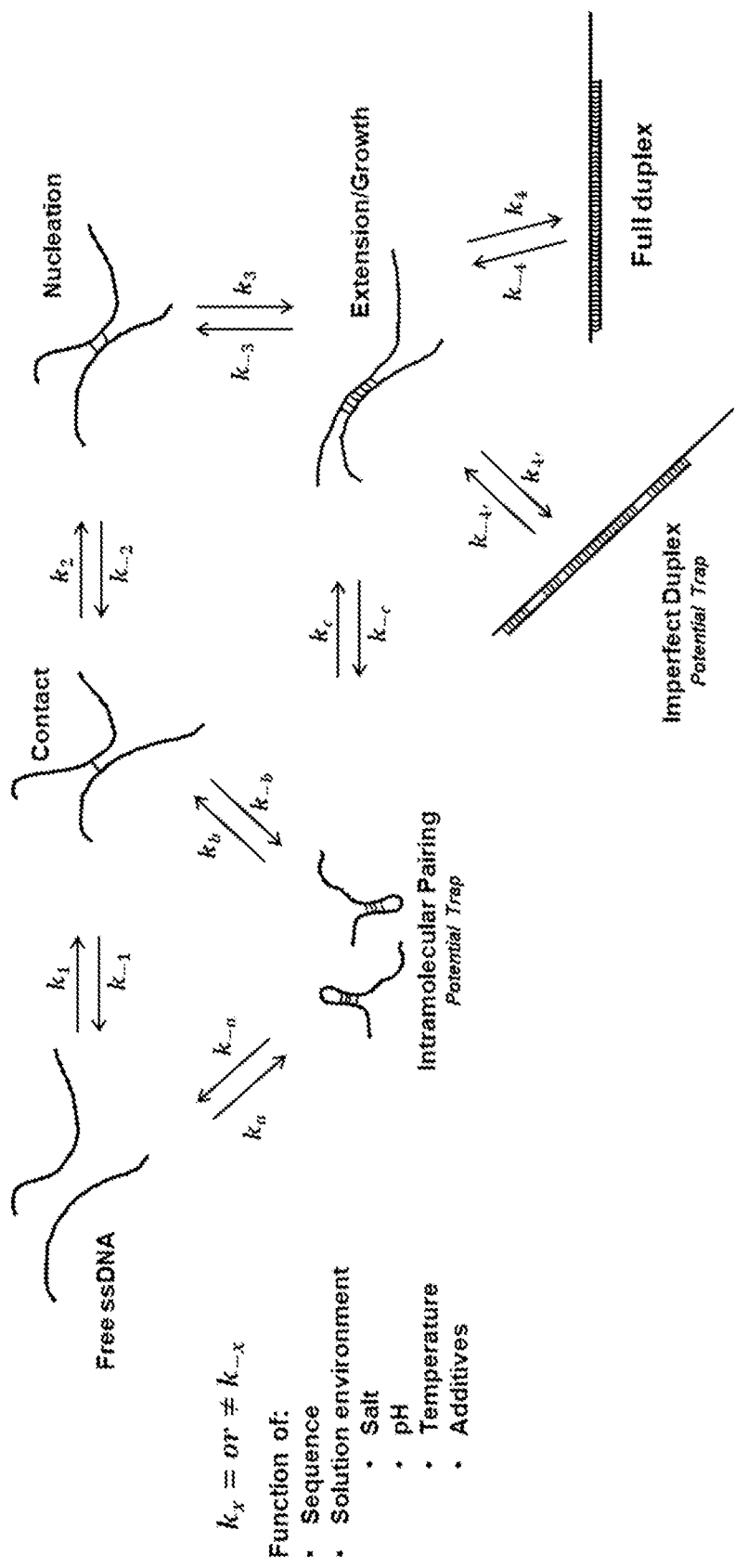
FIG. 1 shows a schematic of the factors affecting hybridization of single-stranded DNA with a complementary partner (e.g., a primer or probe). In complex systems, kinetics are important. Achieving on-target duplexes by hybridization is typically slow. Using the melting step after capturing targets simplifies the workflow while increasing specificity, enhancing yields, and reducing size bias. The system is tunable by increasing the melting step temperature to increase GC-rich sequences.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Representative compositions, methods, and materials are described herein, although equivalent materials and methods can be used in practice.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the phrase "room temperature," "RT," or "ambient temperature" indicates a temperature of about 20-27° C.; about 25° C.±10%; or ~25° C., at standard atmospheric pressure.

As used herein, the term "overnight" refers to a period of time between about 12 hours and about 20 hours. In one aspect, overnight refers to a period of between about 14 hours and about 18 hours. In another aspect, overnight refers to a period of about 16 hours. In another aspect, overnight refers to the period of time from starting the hybridization incubation on one day and then terminating the hybridization incubation on the subsequent day.

As used herein, the term "hybridization" refers to the process of combining two complementary single-stranded nucleic acid molecules and allowing them to form a single double-stranded hybrid molecule through base pairing.

As used herein, the term "melt" refers to the process of heating a sample of on-target and off-target double-stranded nucleic acid molecules to a temperature high enough to specifically disassociate the off-target double-stranded nucleic acid molecule into two separate single-stranded nucleic acid molecules.

As used herein, the term "additive" refers to one or more components added to the buffers described herein to enhance hybridization and improve overall specificity.

As used herein, the terms "standard" or "conventional" refer to typical targeted sequencing hybridization-capture methods. In one aspect, the standard method is the xGEN targeted sequencing hybridization-capture method (Integrated DNA Technologies, Coralville, IA).

As used herein, the term "target enrichment" with respect to a nucleic acid is intended to refer to increasing the relative concentration of particular nucleic acid species in the sample.

As used herein, the term "nucleic acid" may refer to DNA, RNA, dsDNA, dsRNA, ssDNA, ssRNA, or hybrids of DNA/RNA complexes or sequences obtained from any source, containing target and non-target sequences. For example, a nucleic acid sample can be obtained from artificial sources or by chemical synthesis, or from viruses, prokaryotic cells including microbes, or eukaryotic cells. Biological samples may be vertebrate, including human or excluding humans, invertebrates, plants, microbes, viruses, mycoplasma, fungi, or Archaea.

A nucleic acid sample may comprise whole genomic sequences, portions of the genomic sequence, chromosomal sequences, mitochondrial sequences, PCR products, whole genome amplification products or products of other amplification protocol, such as but not limited to, cDNA sequences, mRNA sequences, whole transcriptome sequences, exons, or intronic. These examples are not to be construed as limiting the sample types applicable to aspects described herein.

Described herein are methods and compositions for improved hybridization capture for enriching for target nucleic acid sequences from a population of nucleic acids. The method includes: combining in solution a population of nucleic acids and a complementary probe set; permitting the complementary probe set to hybridize or bind to the target nucleic acid; selectively immobilizing the probe/target nucleic acid complex; exposing the selectively immobilized probe/target nucleic acid complex to a temperature below the aggregate $T_m$ to melt unwanted non-target material. Washing the complex to remove the unbound non-target material enriching for target nucleic acid.

One embodiment described herein is a method for hybridization capture. In one aspect an on-bead melt step is described. Instead of assuming hyb-capture probe-target association reaches equilibrium and follows the same kinetics as probe-target dissociation (melt) as existing hybridization-capture methods, the method disclosed herein directly uses $T_m$/dissociation/melt as the key hybridization capture qualifier. After a hybridization-capture incubation, biotinylated probes are bound to streptavidin beads at low temperature. The target-probe-bead complex is then heated or "melted" at or just below an aggregate $T_m$ to remove non-specific and unwanted non-target material. This is expected to occur relatively quickly as it should follow simple dissociation kinetics. The method only involves "melting" of duplexes and diffusion of the free non-target into solution. A distinguishing feature of the disclosed approach is to perform the "capture" step prior to the "melt" step.

In one embodiment, the method simplifies the workflow of hybridization capture by combining the melt-removal of the off-target hybridizations with the probe-capture by immobilized streptavidin. During the melt incubation, biotin-probes continue to bind the streptavidin beads and the probe-target capture continues. Additionally, the method incorporates a melt step that replaces long hands-on capture steps with short room temperature incubation with mixing on an orbital or rotary shaker.

Another embodiment described herein is specific buffer compositions that have been optimized to increase specificity and stringency in the methods described herein. The buffer compositions comprise buffers, salts, detergents, and additives that decrease $T_m$ dependence on double stranded target GC base content to improve the capture. With the addition of certain additives all probe target $T_m$s of the complex sample converge to a narrow range. In one aspect, optimum types and levels of additives are determined for each hyb-capture application and probe design for increased on-target and uniformity performance. In another aspect, incubation at lower temperature of the pre-determined range during the melt step increases on-target to off-target ratio of the captured target nucleic acid. In another aspect, the simplified workflow further improves $T_m$ dependence and reduces bias to GC content of dsDNA content to take advantage of $T_m$-converging additives.

Another embodiment described herein is a hybridization capture system. The hybridization capture method is a Hyb-Capture-Melt workflow. In a first step a probe panel is contacted with a nucleic acid sample under conditions to promote hybridization. Optionally, the probe panel may contain a capture moiety, for example, but not limited to biotinylation. The biotinylated probes are complementary to target nucleic acids or nucleic acids to be enriched for. In the first step the goal is to increase the hybridization capture yield. Specificity of the nucleic acid capture is secondary to yield. In a second step the biotinylated probes are immobilized to streptavidin beads. Probes with and without hybridized targets are immobilized. In a third step a melt is performed to dissociate all non-specific hybridization interactions. Without being bound to a single theory it is also expected that after the melt is performed re-hybridization of captured probes with target sequence occurs, further improving both yield and specificity. In a fourth step a wash step is performed to further remove un-hybridized and weakly hybridized non-targeted nucleic acids.

Another embodiment is improved compositions for hybridization capture. In one aspect, hybridization capture buffers are provided that improve the hybridization capture efficiency. In another aspect, $T_m$ modifying reagents may be added. In another aspect, additives that decrease $T_m$ dependence on double stranded target GC base content may be added to improve capture.

Another embodiment is a method for hybridization capture. In one step a hybridization at low stringency is provided. In another step capture (immobilization) is performed at a temperature sufficient to promote immobilization. In another step a melt is performed at an elevated temperature to reduce off-target hybridization. In another step a wash is performed to reduce off-target hybridization and optionally this wash step may be in the absence of a hot-wash.

One embodiment described herein is a method for enrichment of a population of nucleic acid target sequences in a sample comprising: (a) providing a sample of nucleic acid molecules comprising a plurality of target nucleic acid sequences and a plurality of off-target nucleic acid sequences; (b) hybridizing the sample to a panel of nucleic acid probes that are complementary to the plurality of target nucleic acid sequences under hybridization conditions to generate a probe/target complex; (c) selectively immobilizing the probe/target complex to form an immobilized probe/target complex; (d) heating the immobilized probe/target complex to a temperature at or below the aggregate $T_m$ of the probe/target complex for a period of time sufficient to disassociate the off-target nucleic acid sequences; and (e) washing the immobilized probe/target complex to remove non-hybridized nucleic acid sequences and off-target nucleic acid sequences from the hybridized plurality of target nucleic acid sequences, thereby enriching for the plurality of target nucleic acid sequences in the sample. In one aspect, the panel of nucleic acid probes that are complementary to the plurality of target nucleic acid sequences further comprises a capture moiety. In another aspect, the capture moiety is biotin. In another aspect, the hybridization conditions comprise a hybridization buffer comprising one or more of: (a) salts selected from one or more of monovalent, divalent, sodium, ammonium, cesium, or manganese, chlorides, citrates, sulfates, perchlorates, isothiocyanates, or guanidinium; (b) chelating agents selected from one or more of ethylenediaminetetraacetic acid (EDTA), ethylene glycol-bis(p-aminoethyl ether)-N,N,N',N'-tetraacetic acid (EGTA), or (1,2-bis(o-aminophenoxy)ethane-N,N,N',N'-tetraacetic acid (BAPTA); (c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate); (d) detergents selected from one or more of sodium dodecylsulfate (SDS), polysorbate 20 (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA). In another aspect, the hybridization buffer contains formamide. In another aspect, the hybridization buffer does not contain formamide.

In one embodiment, the hybridization conditions comprise an incubation time ranging from about 10 minutes to about 48 hours. In one aspect, the hybridization conditions comprise an incubation time ranging from about 2 hours to overnight. In another aspect, equivalent specificity and equivalent yield are achieved with a 2-hour incubation time as compared to an overnight incubation time. In another aspect, the hybridization conditions comprise an incubation temperature ranging from about 55° C. to about 75° C. In another aspect, the hybridization conditions comprise an incubation temperature ranging from about 60° C. to about 70° C. In another aspect, the hybridization conditions comprise an incubation time of about 2 hours and an incubation temperature of about 65° C.

In another embodiment, the probe/target complex is selectively immobilized using streptavidin beads. In one aspect, the probe/target complex is selectively immobilized under conditions comprising an incubation time ranging from about 10 minutes to about 48 hours. In another aspect, the probe/target complex is selectively immobilized under conditions comprising an incubation temperature ranging from 20° C. to 40° C. In another aspect, the probe/target complex is selectively immobilized under conditions comprising an incubation time of about 30 minutes and an incubation temperature of room temperature. In another aspect, the heating of the immobilized probe/target complex comprises a melt buffer comprising one or more of: (a) salts selected from one or more of monovalent, divalent, sodium, ammonium, cesium, or manganese, chlorides, citrates, sulfates, perchlorates, isothiocyanates, or guanidinium; (b) chelating agents selected from one or more of ethylenediaminetetraacetic acid (EDTA), ethylene glycol-bis(p-aminoethyl ether)-N,N,N',N'-tetraacetic acid (EGTA), or (1,2-bis(o-aminophenoxy)ethane-N,N,N',N'-tetraacetic acid (BAPTA); (c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate); (d) detergents selected from one or more of sodium dodecylsulfate (SDS), polysorbate 20 (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

In another embodiment, the heating of the immobilized probe/target complex comprises an incubation time ranging from about 5 minutes to about 1 hour. In one aspect, the heating of the immobilized probe/target complex comprises an incubation temperature ranging from about 50° C. to about 70° C. In another aspect, the heating of the immobilized probe/target complex comprises an incubation time of about 20 minutes and an incubation temperature of about 55° C. In another aspect, the washing of the immobilized probe/target complex comprises two distinct wash buffers, wherein each wash buffer independently comprises one or more of: (a) salts selected from one or more of monovalent, divalent, sodium, ammonium, cesium, or manganese, chlorides, citrates, sulfates, perchlorates, isothiocyanates, or guanidinium; (b) chelating agents selected from one or more of ethylenediaminetetraacetic acid (EDTA), ethylene glycol-bis(p-aminoethyl ether)-N,N,N',N'-tetraacetic acid (EGTA), or (1,2-bis(o-aminophenoxy)ethane-N,N,N',N'-tetraacetic acid (BAPTA); (c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino) ethanesulfonic acid (MES); or dimethylarsenic acid (Cacodylate); (d) detergents selected from one or more of sodium dodecylsulfate (SDS), polysorbate 20 (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

In another embodiment, the washing of the immobilized probe/target complex comprises an incubation time of about 5 minutes to about 15 minutes and an incubation temperature of about 60° C. In one aspect, the method improves specificity and enhances yield as compared to a conventional method. In another aspect, the conventional method does not comprise a step of heating prior to washing. In another aspect, the method improves on-target percentage as compared to a conventional method. In another aspect, the conventional method does not comprise a step of heating prior to washing. In another aspect, the method reduces handling time and throughput time as compared to a conventional method. In another aspect, the conventional method does not comprise a step of heating prior to washing. In another aspect, the method is suitable for automation and reduces complexity as compared to a conventional method. In another aspect, the conventional method does not comprise a step of heating prior to washing.

Another embodiment described herein is a plurality of target nucleic acid sequences isolated using the methods described herein.

Another embodiment described herein is a means for isolating a plurality of target nucleic acid sequences comprising any of the means, methods, steps, or compositions described herein.

Another embodiment described herein is the use of the methods described herein to isolate a plurality of target nucleic acid sequences.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

Various embodiments and aspects of the inventions described herein are summarized by the following clauses:

Clause 1. A method for enrichment of a population of nucleic acid target sequences in a sample comprising:
  (a) providing a sample of nucleic acid molecules comprising a plurality of target nucleic acid sequences and a plurality of off-target nucleic acid sequences;
  (b) hybridizing the sample to a panel of nucleic acid probes that are complementary to the plurality of target nucleic acid sequences under hybridization conditions to generate a probe/target complex;
  (c) selectively immobilizing the probe/target complex to form an immobilized probe/target complex;
  (d) heating the immobilized probe/target complex to a temperature at or below the aggregate $T_m$ of the probe/target complex for a period of time sufficient to disassociate the off-target nucleic acid sequences; and
  (e) washing the immobilized probe/target complex to remove non-hybridized nucleic acid sequences and off-target nucleic acid sequences from the hybridized plurality of target nucleic acid sequences, thereby enriching for the plurality of target nucleic acid sequences in the sample.

Clause 2. The method of clause 1, wherein the panel of nucleic acid probes that are complementary to the plurality of target nucleic acid sequences further comprises a capture moiety.

Clause 3. The method of clause 2, wherein the capture moiety is biotin.

Clause 4. The method of any one of clauses 1-3, wherein the hybridization conditions comprise a hybridization buffer comprising one or more of:
  (a) salts selected from one or more of monovalent, divalent, sodium, ammonium, cesium, or manganese, chlorides, citrates, sulfates, perchlorates, isothiocyanates, or guanidinium;
  (b) chelating agents selected from one or more of ethylenediaminetetraacetic acid (EDTA), ethylene glycol-bis(β-aminoethyl ether)-N,N,N',N'-tetraacetic acid (EGTA), or (1,2-bis(o-aminophenoxy) ethane-N,N,N',N'-tetraacetic acid (BAPTA);

(c) buffering agents selected from one or more of tris(hydroxymethyl)aminomethane (Tris); 2-(bis(2-hydroxyethyl)amino)acetic acid) (Bicine); (N-[tris (hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate);

(d) detergents selected from one or more of sodium dodecylsulfate (SDS), polysorbate (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

Clause 5. The method of any one of clauses 1-4, wherein the hybridization buffer contains formamide.

Clause 6. The method of any one of clauses 1-4, wherein the hybridization buffer does not contain formamide.

Clause 7. The method of any one of clauses 1-6, wherein the hybridization conditions comprise an incubation time ranging from about 10 minutes to about 48 hours.

Clause 8. The method of any one of clauses 1-7, wherein the hybridization conditions comprise an incubation time ranging from about 2 hours to overnight.

Clause 9. The method of any one of clauses 1-8, wherein equivalent specificity and equivalent yield are achieved with a 2-hour incubation time as compared to an overnight incubation time.

Clause 10. The method of any one of clauses 1-9, wherein the hybridization conditions comprise an incubation temperature ranging from about 55° C. to about 75° C.

Clause 11. The method of any one of clauses 1-10, wherein the hybridization conditions comprise an incubation temperature ranging from about 60° C. to about 70° C.

Clause 12. The method of any one of clauses 1-11, wherein the hybridization conditions comprise an incubation time of about 2 hours and an incubation temperature of about 65° C.

Clause 13. The method of any one of clauses 1-12, wherein the probe/target complex is selectively immobilized using streptavidin beads.

Clause 14. The method of any one of clauses 1-13, wherein the probe/target complex is selectively immobilized under conditions comprising an incubation time ranging from about 10 minutes to about 48 hours.

Clause 15. The method of any one of clauses 1-14, wherein the probe/target complex is selectively immobilized under conditions comprising an incubation temperature ranging from about 20° C. to about 40° C.

Clause 16. The method of any one of clauses 1-15, wherein the probe/target complex is selectively immobilized under conditions comprising an incubation time of about 30 minutes and an incubation temperature of room temperature.

Clause 17. The method of any one of clauses 1-16, wherein the heating of the immobilized probe/target complex comprises a melt buffer comprising one or more of:

(a) salts selected from one or more of monovalent, divalent, sodium, ammonium, cesium, or manganese, chlorides, citrates, sulfates, perchlorates, isothiocyanates, or guanidinium;

(b) chelating agents selected from one or more of ethylenediaminetetraacetic acid (EDTA), ethylene glycol-bis(β-aminoethyl ether)-N,N,N',N'-tetraacetic acid (EGTA), or (1,2-bis(o-aminophenoxy) ethane-N,N,N',N'-tetraacetic acid (BAPTA);

(c) buffering agents selected from one or more of tris(hydroxymethyl)aminomethane (Tris); 2-(bis(2-hydroxyethyl)amino)acetic acid) (Bicine); (N-[tris (hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate);

(d) detergents selected from one or more of sodium dodecylsulfate (SDS), polysorbate (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

Clause 18. The method of any one of clauses 1-17, wherein the heating of the immobilized probe/target complex comprises an incubation time ranging from about 5 minutes to about 1 hour.

Clause 19. The method of any one of clauses 1-18, wherein the heating of the immobilized probe/target complex comprises an incubation temperature ranging from about 50° C. to about 70° C.

Clause 20. The method of any one of clauses 1-19, wherein the heating of the immobilized probe/target complex comprises an incubation time of about 20 minutes and an incubation temperature of about 55° C.

Clause 21. The method of any one of clauses 1-20, wherein the washing of the immobilized probe/target complex comprises two distinct wash buffers, wherein each wash buffer independently comprises one or more of:

(a) salts selected from one or more of monovalent, divalent, sodium, ammonium, cesium, or manganese, chlorides, citrates, sulfates, perchlorates, isothiocyanates, or guanidinium;

(b) chelating agents selected from one or more of ethylenediaminetetraacetic acid (EDTA), ethylene glycol-bis(β-aminoethyl ether)-N,N,N',N'-tetraacetic acid (EGTA), or (1,2-bis(o-aminophenoxy)ethane-N,N,N',N'-tetraacetic acid (BAPTA);

(c) buffering agents selected from one or more of tris(hydroxymethyl)aminomethane (Tris); 2-(bis(2-hydroxyethyl)amino)acetic acid) (Bicine); (N-[tris(hydroxymethyl)methyl]glycine (Tricine); [tris(hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl]amino]ethanesulfonic acid (TES); 3-(N-morpholino)propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate);

(d) detergents selected from one or more of sodium dodecylsulfate (SDS), polysorbate (Tween® 20), octyl phenol ethoxylate (Triton X-100), octylphenoxypolyethoxyethano (IGEPAL®-CA 630), nonyl phenoxypolyethoxylethanol (NP-40), or cetrimonium bromide (CTAB); or (e) additives selected from one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

Clause 22. The method of any one of clauses 1-21, wherein the washing of the immobilized probe/target complex comprises an incubation time of about 5 minutes to about 15 minutes and an incubation temperature of about 60° C.

Clause 23. The method of any one of clauses 1-22, wherein the method improves specificity and enhances yield as compared to a conventional method.

Clause 24. The method of any one of clauses 1-23, wherein the conventional method does not comprise a step of heating prior to washing.

Clause 25. The method of any one of clauses 1-24, wherein the method improves on-target percentage as compared to a conventional method.

Clause 26. The method of any one of clauses 1-25, wherein the conventional method does not comprise a step of heating prior to washing.

Clause 27. The method of any one of clauses 1-26, wherein the method reduces handling time and throughput time as compared to a conventional method.

Clause 28. The method of any one of clauses 1-27, wherein the conventional method does not comprise a step of heating prior to washing.

Clause 29. The method of any one of clauses 1-28, wherein the method is suitable for automation and reduces complexity as compared to a conventional method.

Clause 30. The method of any one of clauses 1-29, wherein the conventional method does not comprise a step of heating prior to washing.

Clause 31. A plurality of target nucleic acid sequences isolated using the methods of any one of clauses 1-30.

Clause 32. A means for isolating a plurality of target nucleic acid sequences comprising any of the methods of clauses 1-30.

Clause 33. Use of the method of any one of clauses 1-30 to isolate a plurality of target nucleic acid sequences.

REFERENCES

Yin and Zhao, "Kinetics and Dynamics of DNA Hybridization," *Acc. Chem. Res.* 44(11): 1172-1181 (2011).

Wang et al., "Direct and sensitive miRNA profiling from low-input total RNA," *RNA* 13(1): 151-159 (2007).

Grenwedel and Hsu, "Salt effects on the denaturation of DNA," *Biopolymers* 7(4): 557-570 (1969) Melchior and Von Hippel, "Alteration of the Relative Stability of dA•dT and dG•dC Base Pairs in DNA," *Proc. Nat. Acad. Sci. USA* 70(2): 298-302 (1973).

Grenwedel et al., "The effects of aqueous neutral-salt solutions on the melting temperatures of deoxyribonucleic acids," *Biopolymers* 10(1):47-68 (1971).

Vaduevamurthy et al., "Betaine structure and the presence of hydroxyl groups alters the effects on DNA melting temperatures," *Biopolymers* 91(1): 85-94 (2008).

EXAMPLES

Example 1

This example demonstrates improved performance of hybridization capture with the addition of a melt step during probe/target complex immobilization. Using Integrated DNA Technologies, Inc., target capture protocol as an example, hybridization-capture was performed with either 2-hour or overnight hybridization with hybridization incubation occurring at 65-70° C. Additionally, the hybridization buffer either contained formamide (+Form) or did not contain formamide (−Form). The target capture panel used contains 18,815 biotinylated targeting probes and was hybridized with 250 ng capture input NA12878 gDNA library. Four replicates at each hybridization temperature and condition were performed. Following hybridization capture the hybridized probe/target complex were incubated with streptavidin beads following the IDT method "xGen for hybridization capture of DNA libraries" 2020 (Integrated DNA Technologies, Coralville, IA; "SOP", which is incorporated by reference herein for such teachings) or treated with a simple-bind and melt step (Simple Bind-Melt at 65° C.) as indicated.

Figure 9:
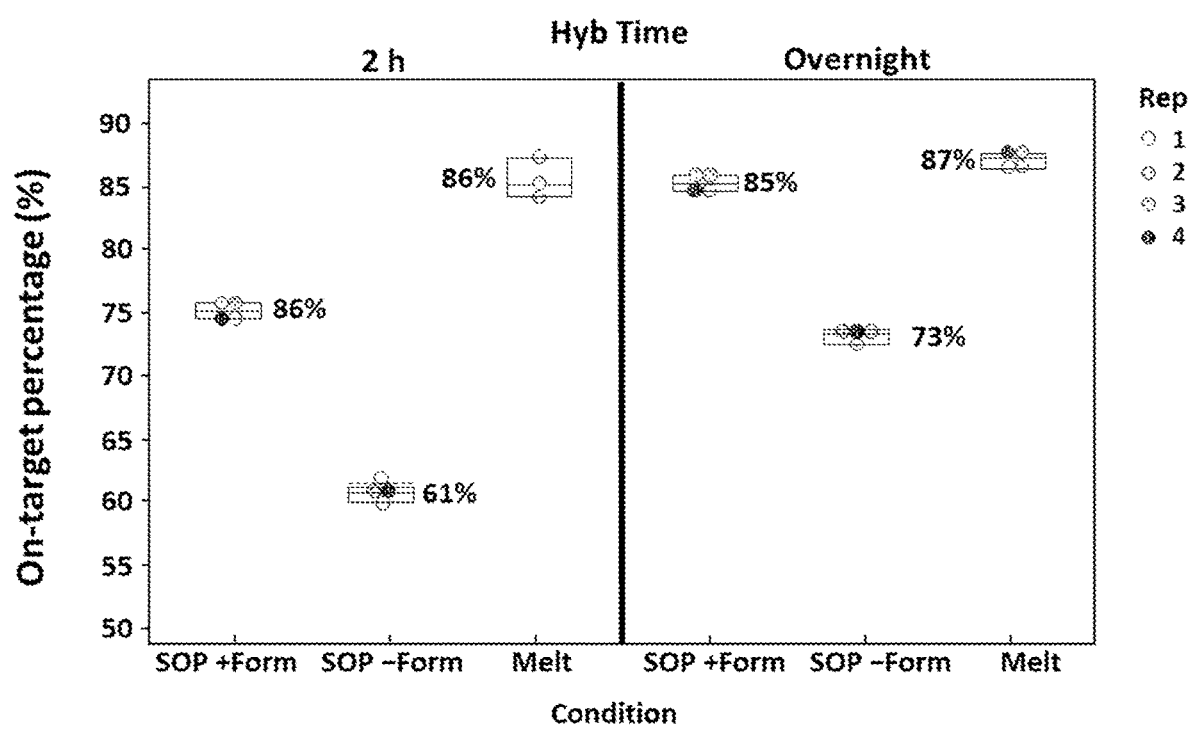
FIG. 9 shows a comparison of the on-target percentage of 2-hour and overnight hybridization captures under standard conditions (SOP +Form), standard conditions without formamide in the hybridization buffer (SOP –Form), and with Melt-Simple bind step.

As shown in FIG. 9 the addition of a Melt step (Melt-Simple Bind) after the capture to streptavidin beads increased the On-Target percentage for both the 2-hour and overnight hybridization incubation. With the addition of the melt step during immobilization the on-target percentage for the 2-hour hybridization increased from 75% (SOP +Form) to 86%. The addition of the melt step to the immobilization for the overnight hybridization reactions increased the on-target percentage from 85% (SOP +Form) to 87% (Melt).

Figure 10:
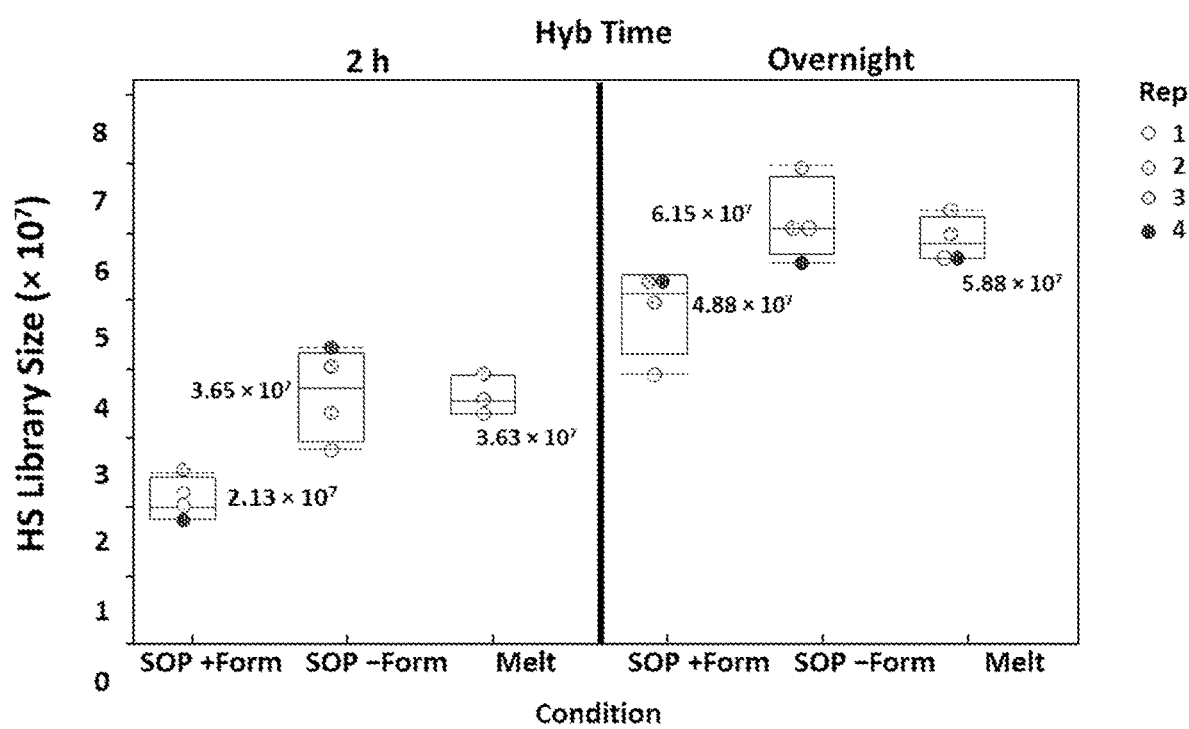
FIG. 10 shows a comparison of the HS_LIBRARY_SIZE of 2-hour and overnight hybridization captures under standard conditions (SOP +Form), standard conditions without formamide in the hybridization buffer (SOP –Form), and with Melt-Simple bind step.

FIG. 10 demonstrates that the addition of a melt step during the bead capture improves the HS_LIBRARY_SIZE for both 2-hour hybridization and overnight hybridization incubations. With the addition of the melt step during immobilization the HS_LIBRARY_SIZE increased from $2.13 \times 10^7$ (SOP +Form) to $3.63 \times 10^7$ (Melt) for the 2-hour hybridization incubation. Furthermore, with the addition of the melt step during immobilization the HS_LIBRARY_SIZE increased from $4.88 \times 10^7$ (SOP +Form) to $5.88 \times 10^7$ (Melt) for the overnight incubation. With the addition of the melt step during immobilization the HS_LI- BRARY_SIZE for both the SOP –Form and Melt conditions remained similar at the 2 hour and overnight hybridization incubations.

Figure 11:
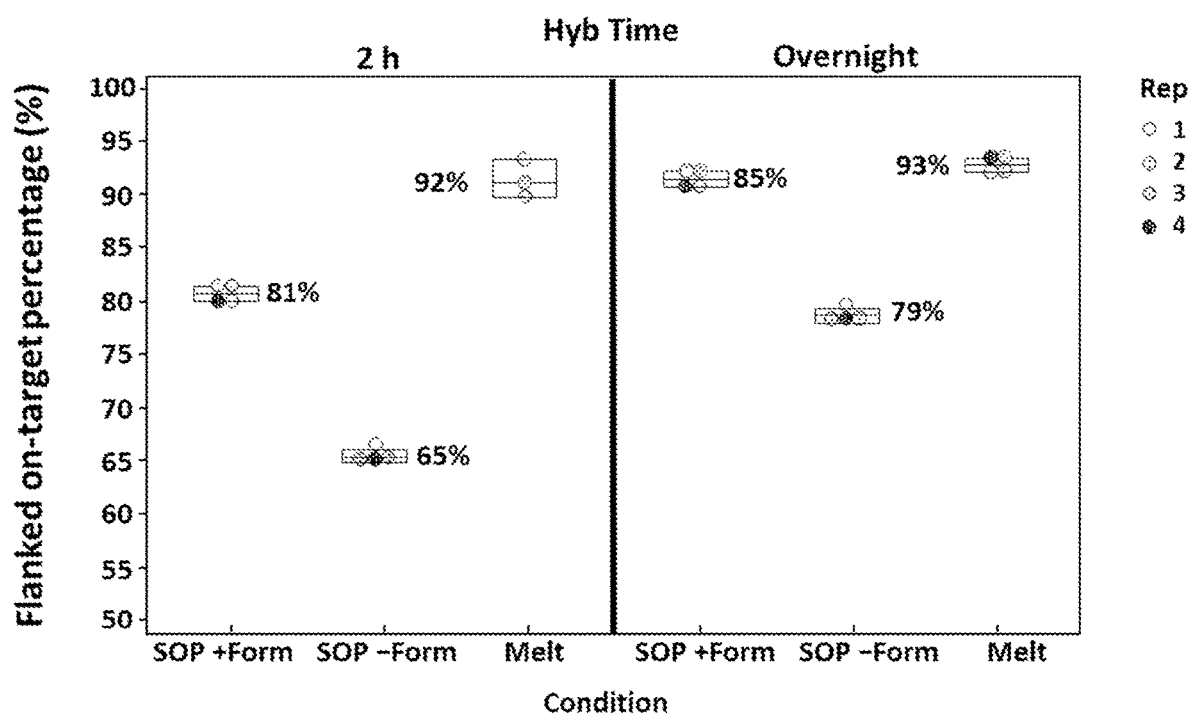
FIG. 11 shows a comparison of the Flanked-on target percentage of 2-hour and overnight hybridization captures under standard conditions (SOP +Form), standard conditions without formamide in the hybridization buffer (SOP –Form), and with Melt-Simple bind step.

FIG. 11 shows that the addition of a melt step during the bead capture improves the Flanked on-target percentage for both 2-hour and overnight hybridization incubation. With the addition of the melt step during immobilization the flanked on-target percentage for the 2-hour hybridization increased from 81% (SOP +Form) and 65% (SOP –Form) to 92% (Melt). The addition of the melt step to the immobilization for the overnight hybridization incubation was also improved. The flanked on-target percentage for the overnight hybridization increased from 92% (SOP +Form) and 79% (SOP –Form) to 93% (Melt).

Figure 12:
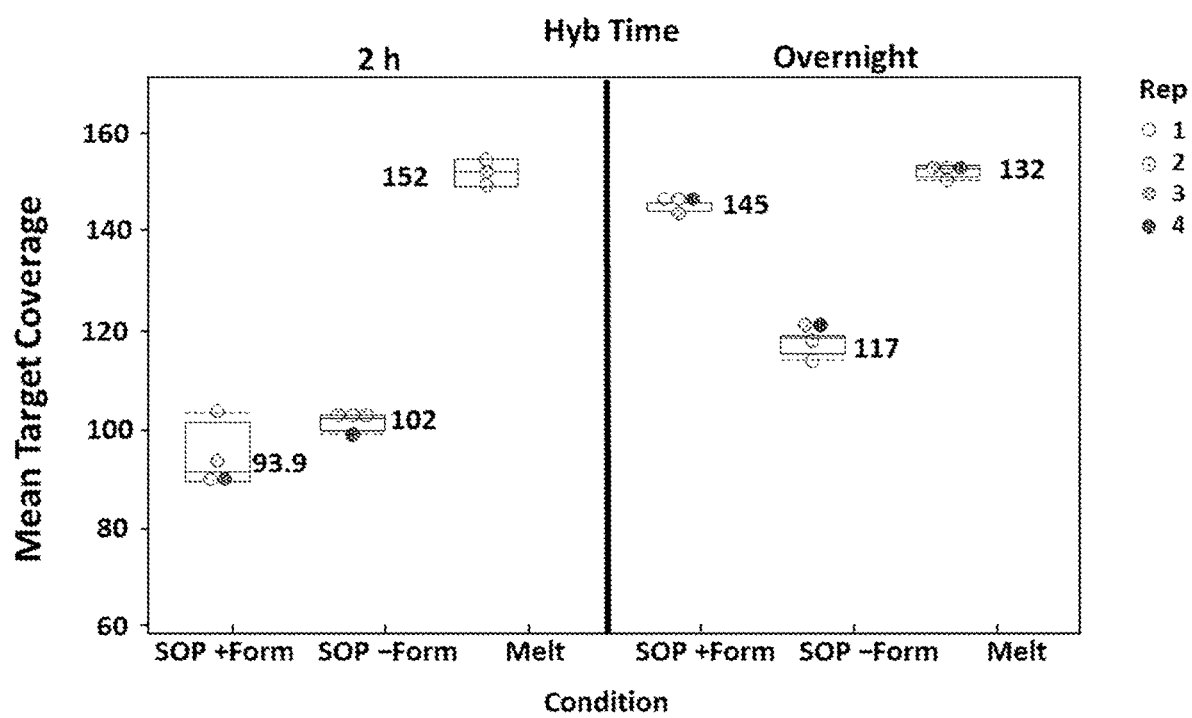
FIG. 12 shows a comparison of the MEAN_TARGET_COVERAGE of 2-hour and overnight hybridization captures under standard conditions (SOP +Form), standard conditions without formamide in the hybridization buffer (SOP –Form), and with Melt-Simple bind step.

FIG. 12 shows that the addition of a melt step during the bead capture improves the MEAN_TARGET_COVERAGE for both the 2 hour and overnight hybridization incubation. With the addition of a melt step during immobilization the MEAN_TARGET_COVERAGE for the 2-hour hybridization increased form 93.9 (SOP +Form) and 102 (SOP –Form) to 152 (Melt). Furthermore, the addition of the melt step to the immobilization for the overnight hybridization incubation was improved. The MEAN_TARGET_COVERAGE for the overnight hybridization incubation increased from 145 (SOP +Form) and 117 (SOP –Form) to 152 (Melt).

Figure 13:
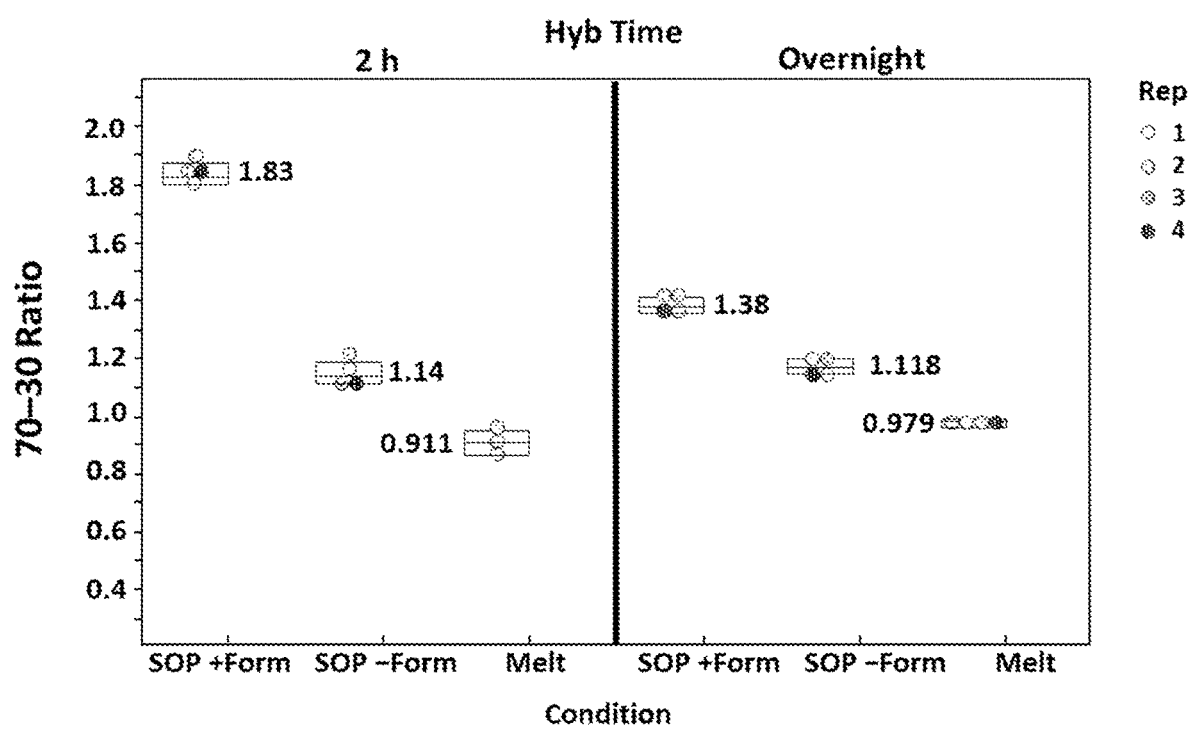
FIG. 13 shows a comparison of the 70-30 ratio of 2-hour and overnight hybridization captures under standard conditions (SOP +Form), standard conditions without formamide in the hybridization buffer (SOP –Form), and with Melt-Simple bind step.

FIG. 13 shows the 70-30 Ratio which is a measure of GC skew in the reads by sequencer. The 70-30 ratio is often used to evaluate potential sequence bias in the library prep process, but it also reflects the sequence content of the target. For the capture panel used in this example the true unbiased ratio is expected to be 0.8-1.0. As is demonstrated, the addition of the melt step during immobilization improves the 70-30 ratio for both the 2-hour and overnight hybridization incubation. FIG. 13 shows that for the 2-hour hybridization the 70-30 ratio dropped from 1.83 (SOP +Form) and 1.14 (SOP –Form) to 0.0.911 (Melt). Additionally, for the overnight hybridization incubation the 70-30 ratio dropped from 1.38 (SOP +Form) and 1.18 (SOP –Form) to 0.929 (Melt).

Example 2

Figure 5:
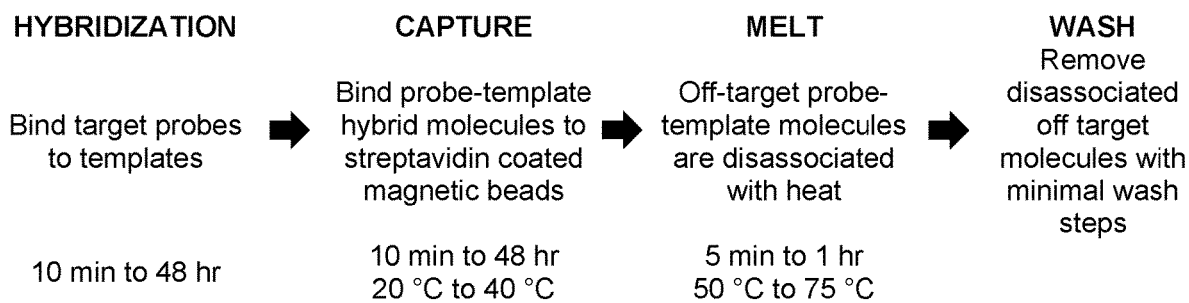
FIG. 5 shows a diagram of the simplified "melt' hybridization capture workflow with exemplary times and temperatures at each step.
Figure 6:
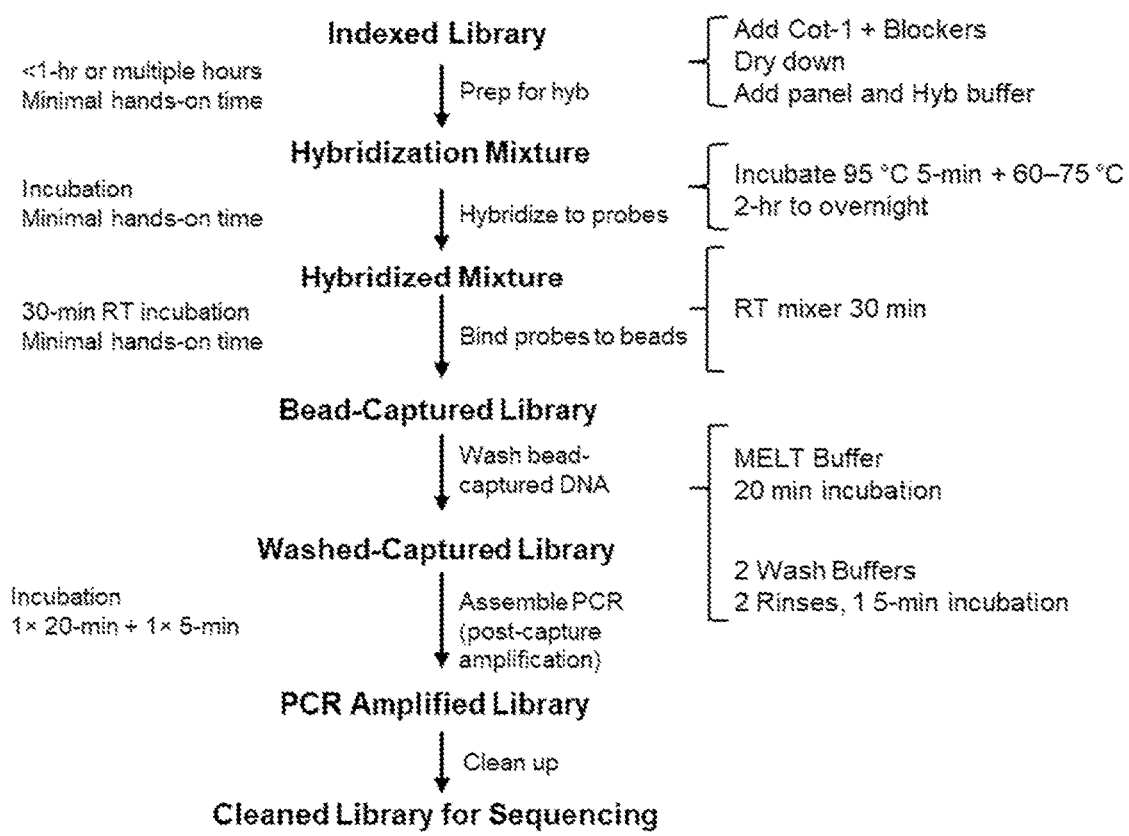
FIG. 6 shows a schematic of a workflow for preparation of a library for sequencing using the simplified "melt' hybridization capture workflow and describes exemplary parameters at each step.
Figure 7A:
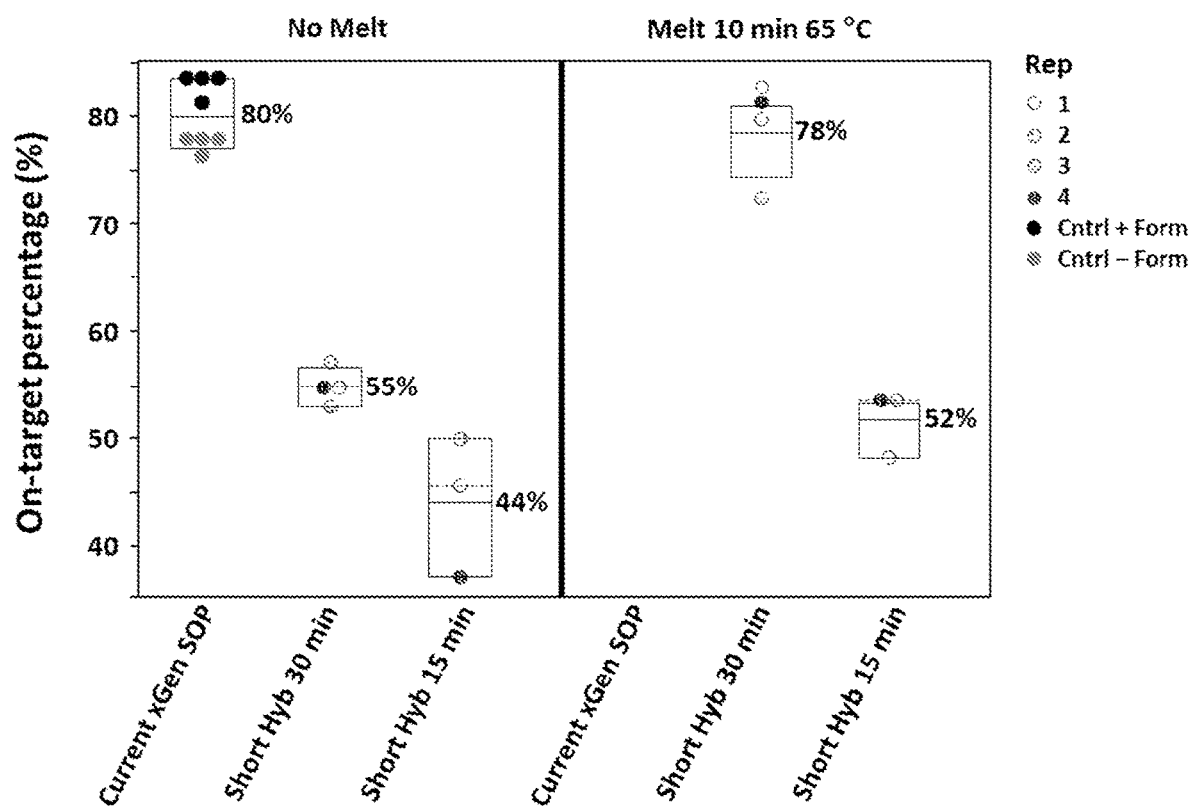
FIGS. 7A and 7B show a comparison of a standard hybridization capture method (xGEN SOP) or the simplified "melt' hybridization (Short Hyb) capture method using 24-hour, 30 minute, or 15 min hybridization incubations at 65° C.
Figure 7B:
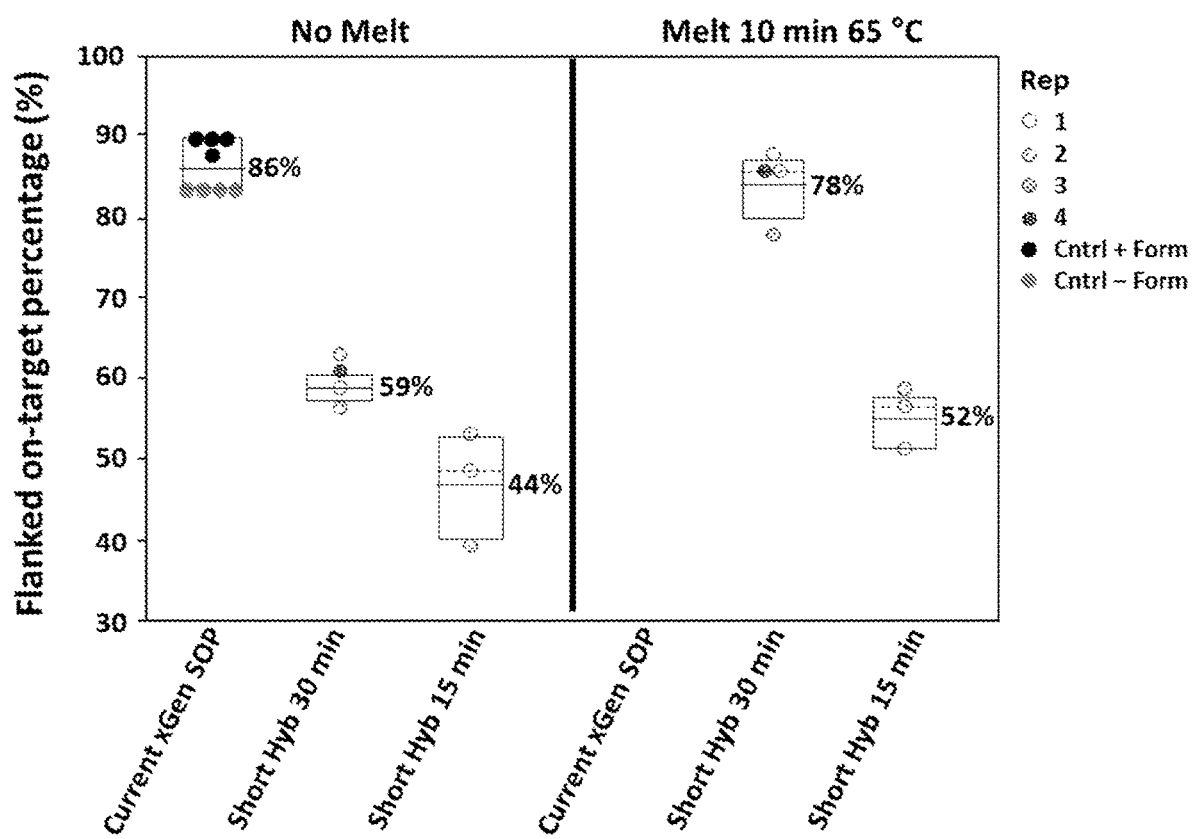
Figure 8A:
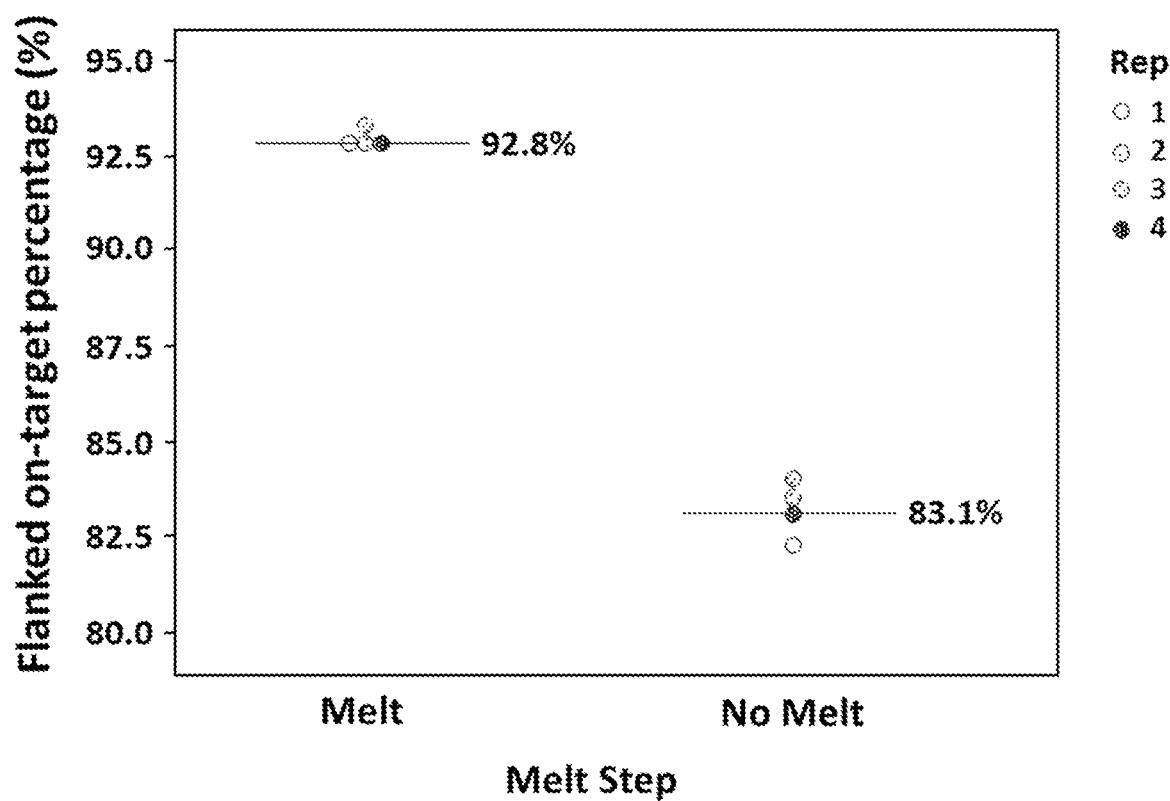
FIGS. 8A and 8B show a comparison of overnight hybridization-capture methods with and without the "Melt-Simple" step.
Figure 8B:
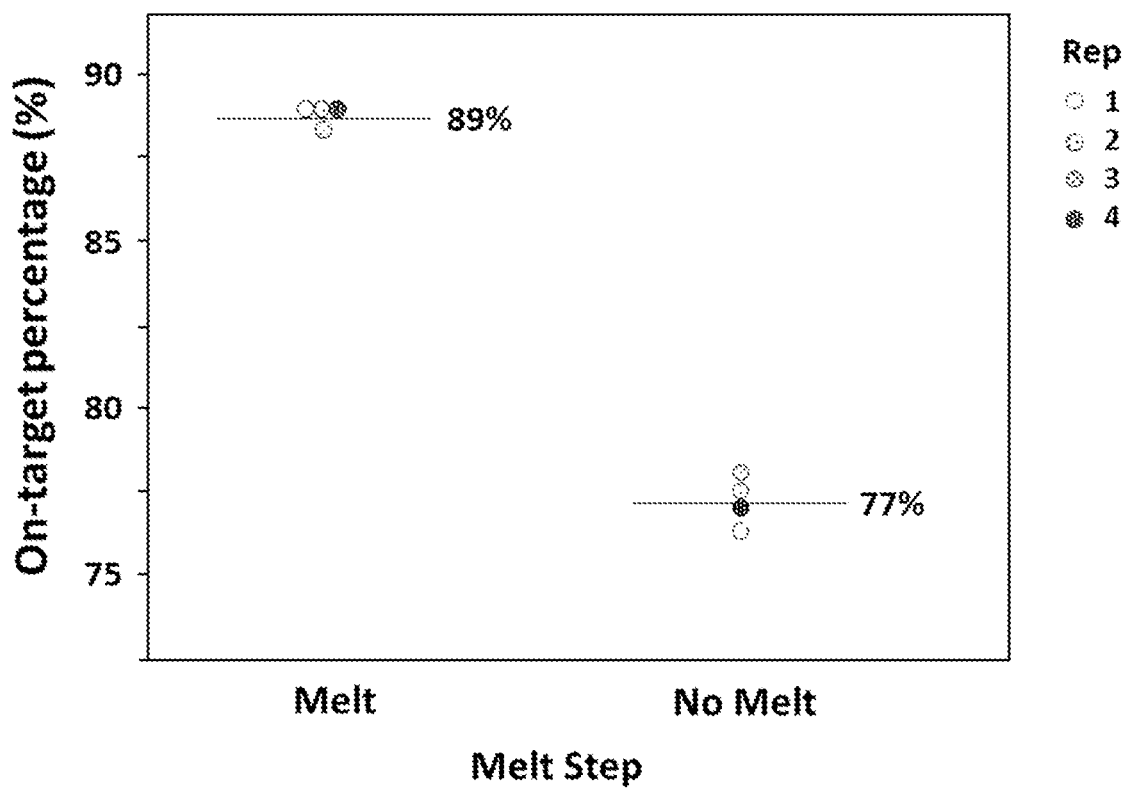

The workflow for preparation of a library for sequencing using the simplified hybridization target capture method (also called Melt-Simple or Hyb V2 herein) are shown in FIG. 4-6. A comparison of the complexity of a standard workflow (as shown in FIG. 1-3) (e.g., xGEN hybridization capture, IDT) is exemplified by Table 1.

TABLE 1

Comparison of IDT xGEN method to Melt-Simple (Hyb V2)

| Steps | xGen | Melt Simple (Hyb V2) |
|---|---|---|
| Buffers to Mix | 8 | ≤4 |
| Hands-on Steps | 17 | 9 |
| Hot-handling on Thermocycler | 7 | 0 |
| Hot-temperature/time sensitive steps | 7 | 0 |
| Hot Buffers | 3 | 0 |
| Incubations | 6 | 3 |
| Total Incubation Time | 61 | 55 |
| Dedicated Time (hands-on/present for step) | 61 | 5 |
| Estimated Total Allocation Time for Experienced Operator (32 samples) | 145 min (2 h 25 min) | 95 min (1 h 35 min) |

Example 3

The Melt-Simple or Hyb V2 workflow was compared with the standard xGEN method using multiple probe panels as shown in Table 2 and 3.

TABLE 2

Performance on Multiple Probe Panels

| Panel | Probe Count | Target Size (bp) |
|---|---|---|
| Exome v2 | 415,115 | 34,156,490 |
| Exome v1 | 425,463 | 38,948,175 |
| IDP Full (Inherited Disease Panel) | 116,692 | 11,135,226 |
| Pan Cancer v2.4 | 18,815 | 2,222,516 |
| AML v3 (Acute Myeloid Leukemia) | 11,731 | 1,190,689 |
| Standard 500 | 509 | 42,600 |

TABLE 3

Performance on Multiple Probe Panels

| Library | Panel | Probe Count | Target Size (Bp) | Total probes per panel (pmol) | Indiv. probe per capture (amol) | *Est. Kapa Probe to Trgt. Ratio | *Est. Prism Probe to Trgt. Ratio |
|---|---|---|---|---|---|---|---|
| Kapa | Exome v2 | 415,115 | 34,156,490 | 20 | 50 | 576 | 613 |
| Kapa | Exome v1 | 425,463 | 38,948,175 | 10 | 25 | 281 | 299 |
| Kapa + Prism | IDP | 116,692 | 11,135,226 | 3 | 26 | 307 | 327 |
| Kapa + Prism | AML v3 | 11,731 | 1,190,689 | 3 | 256 | 3,058 | 3,253 |
| Kapa + Prism | Standard 500 | 509 | 42,600 | 3 | 5,894 | 70,483 | 74,979 |

*Specific to the reference libraries shown here

Conversion: 6.6 pg/diploid genome

Assume library with 100% uniform conversion and amplification.

Assume equal-molar probe concentration

Figure 14:
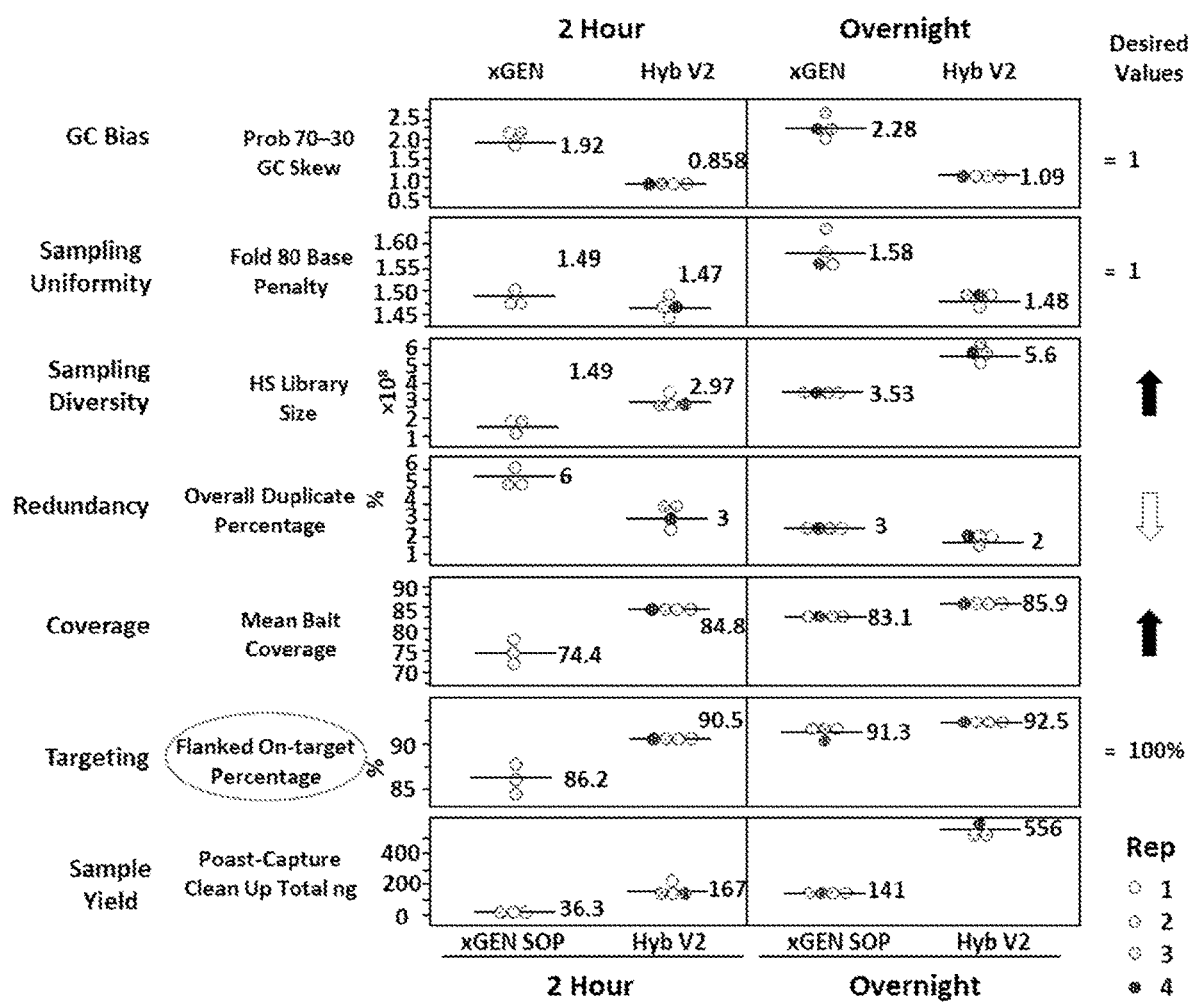
FIG. 14 shows a comparison of the standard hybridization capture method (xGEN) with the Melt-Simple (Hyb V2) method for representative metrics such as GC bias, sampling uniformity, sampling diversity, redundancy, coverage, targeting, and sample yield with 2-hour and overnight hybridization incubations. Results are shown in Tables 4-8.

FIG. 14 shows graphical result of the comparison of Melt-Simple or Hyb V2 workflow was compared with the standard xGEN. For equivalent hybridization time, Melt-Simple or Hyb V2 out-performs xGEN and has high post-capture DNA yields. Table 4 shows comparison ratios.

TABLE 4

Comparison Ratios

| Exome V2 | 2-hr (Hyb V2/xGen) | Overnight (Hyb V2/xGen) |
|---|---|---|
| Probe 70/30 | 0.15* | 0.07 |
| Target 70/30 | 0.19 | 0.06 |
| Uniformity (Fold 80) | 0.95 | 0.82 |
| Sampling Diversity | 2.0 | 1.58 |
| Redundancy | 0.55 | 0.65 |
| Probe Coverage | 1.14 | 1.03 |
| Target Coverage | 1.13 | 1.00 |
| Flanked On-target | 1.05 | 1.01 |
| Total DNA Yield | 4.58 | 3.94 |

$$\text{Ratio: } \frac{\text{Test Condition}}{\text{Standard Condition}} = \frac{\text{Hyb V2 (Melt Simple)}}{\text{xGEN}} = \frac{\text{Hyb V2 Metrics value (or distance from '1')}}{\text{xGEN Metrics value (or Distance from '1')}}$$

*Bold font: Melt Simple (HybV2) is superior to xGEN;
Normal font: Melt Simple (HybV2) is equivalent to xGEN.
Significance thresholds are established from observed variabilities from standard runs.

Tables 5-7 show general parameters comparing Hyb V2 to xGEN at various hybridization times (overnight vs. 2 hours). Table 8 compares 2 hr xGEN to overnight xGEN.

TABLE 5

Comparison Ratios Overnight Hyb V2 vs. Overnight xGEN

|  | Exome V2 | Exome V2 | IDP | AML | Standard 500 |
|---|---|---|---|---|---|
| Probe 70/30 | 0.07 | 0.29 | 0.02 | 0.28 | 0.24 |
| Target 70/30 | 0.06 | 0.29 | 0.01 | 0.26 | *1.60* |
| Uniformity (Fold 80) | 0.82 | 0.67 | 0.86 | 0.82 | 0.88 |
| Sampling Diversity | 1.58 | 1.55 | 1.43 | 1.18 | 1.18 |
| Redundancy | 0.65 | 0.67 | 0.69 | 0.88 | 0.86 |
| Probe Coverage | 1.03 | 1.02 | 1.02 | 1.00 | 0.98 |
| Target Coverage | 1.00 | 1.03 | 1.01 | 0.99 | 1.00 |
| Flanked On-target | 1.01 | 1.01 | 1.03 | 1.01 | 0.99 |
| Total DNA Yield | 3.94 | 5.15 | 2.57 | 5.36 | *0.28* |

$$\text{Ratio: } \frac{\text{Test Condition}}{\text{Standard Condition}} = \frac{\text{Overnight Hyb V2 (Melt Simple)}}{\text{Overnight xGEN}}$$

*Bold font: Melt Simple (HybV2) is superior to xGEN;
Bormal font: Melt Simple (HybV2) is equivalent to xGEN;
Italic font: Melt Simple (HybV2) is inferior to xGEN.

TABLE 6

Comparison Ratios 2-hr Hyb V2 vs. 2-hr xGEN

|  | Exome V2 | Exome V2 | IDP | AML | Standard 500 |
|---|---|---|---|---|---|
| Probe 70/30 | 0.15 | 0.15 | 0.12 | 0.04 | 0.32 |
| Target 70/30 | 0.19 | 0.17 | 0.11 | 0.01 | *3.31* |
| Uniformity (Fold 80) | 0.95 | 0.73 | 0.92 | 0.76 | 0.88 |
| Sampling Diversity | 2.00 | 1.79 | 1.85 | 1.36 | 1.22 |
| Redundancy | 0.55 | 0.59 | 0.64 | 0.76 | 1.13 |
| Probe Coverage | 1.14 | 1.08 | 1.18 | 1.08 | 1.37 |
| Target Coverage | 1.13 | 1.13 | 1.18 | 1.10 | 1.36 |
| Flanked On-target | 1.05 | 1.05 | 1.12 | 1.06 | 1.31 |
| Total DNA Yield | 4.58 | 4.48 | 4.85 | 4.47 | 2.10 |

$$\text{Ratio: } \frac{\text{Test Condition}}{\text{Standard Condition}} = \frac{\text{2 hr Hyb V2 (Melt Simple)}}{\text{2 hr xGEN}}$$

*Bold font: Melt Simple (HybV2) is superior to xGEN;
Normal font: Melt Simple (HybV2) is equivalent to xGEN;
Italic font: Melt Simple (HybV2) is inferior to xGEN.

TABLE 7

Comparison Ratios 2-hr Hyb V2 vs. Overnight xGEN

|  | Exome V2 | Exome V2 | IDP | AML | Standard 500 |
|---|---|---|---|---|---|
| Probe 70/30 | 0.11 | 0.16 | 0.14 | 0.09 | 0.90 |
| Target 70/30 | 0.12 | 0.16 | 0.14 | 0.01 | *2.20* |
| Uniformity (Fold 80) | 0.80 | 0.78 | 1.04 | *1.07* | *1.12* |
| Sampling Diversity | 0.84 | *0.74* | *0.70* | 0.99 | 1.08 |
| Redundancy | *1.19* | *1.33* | *1.44* | 1.00 | 0.96 |
| Probe Coverage | 1.02 | 0.99 | 1.02 | 1.02 | 1.06 |
| Target Coverage | 0.95 | 1.00 | 1.02 | 1.05 | 1.10 |
| Flanked On-target | 0.99 | 0.99 | 1.01 | 0.99 | 1.01 |
| Total DNA Yield | 1.18 | 1.07 | *0.58* | 2.85 | *0.21* |

$$\text{Ratio: } \frac{\text{Test Condition}}{\text{Standard Condition}} = \frac{\text{2 hr Hyb V2 (Melt Simple)}}{\text{Overnight xGEN}}$$

*Bold font: Melt Simple (HybV2) is superior to xGEN;
Normal font: Melt Simple (HybV2) is equivalent to xGEN;
Italic font: Melt Simple (HybV2) is inferior to xGEN.

TABLE 8

Comparison Ratios 2-hr xGEN vs. Overnight xGEN

|  | Exome V2 | Exome V2 | IDP | AML | Standard 500 |
|---|---|---|---|---|---|
| Probe 70/30 | 0.72 | *1.06* | *1.22* | *2.35* | *2.79* |
| Target 70/30 | 0.64 | 0.97 | *1.24* | *2.13* | 0.67 |
| Uniformity (Fold 80) | 0.84 | *1.08* | *1.14* | *1.40* | *1.27* |
| Sampling Diversity | *0.42* | *0.41* | *0.38* | *0.73* | 0.89 |
| Redundancy | *2.15* | *2.25* | *2.25* | *1.31* | 0.86 |
| Probe Coverage | *0.90* | *0.92* | *0.87* | *0.95* | *0.77* |
| Target Coverage | *0.84* | *0.89* | *0.87* | *0.96* | *0.81* |
| Flanked On-target | *0.94* | *0.94* | *0.90* | *0.94* | *0.77* |
| Total DNA Yield | *0.26* | *0.24* | *0.12* | *0.64* | *0.10* |

$$\text{Ratio: } \frac{\text{Test Condition}}{\text{Standard Condition}} = \frac{\text{2 hr xGEN}}{\text{Overnight xGEN}}$$

*Bold font: 2 hr xGEN is superior to ON xGEN;
Normal font: 2 hr xGEN is is equivalent to xGEN;
Italic font: 2 hr xGEN is inferior to xGEN.

These results show that the simplified Hyb V2 workflow does not negatively impact performance and Hyb V2 has better performance with short hybridization targets.

Example 4

The simplified Hyb V2 workflow with hybridization to equivalently prepared Prism and Kapa Libraries was compared to xGEN using the IDP, AML and Standard 500 probe sets. Results are shown in Tables 9-11.

TABLE 9

Comparison Ratios for Equivalently prepared Prism and Kapa Libraries

| IDP | xGEN: Prism/Kapp | Prism/Hyb V2/xGEN | Prism Hyb V2/Kapp xGEN |
|---|---|---|---|
| Probe 70/30 | 2.03 | 0.06 | 0.11 |
| Target 70/30 | 2.09 | 0.06 | 0.12 |
| Uniformity (Fold 80) | 1.23 | 0.72 | 0.88 |
| Sampling Diversity | *0.78* | 1.50 | 1.18 |
| Redundancy | *1.36* | 0.65 | 0.89 |
| Probe Coverage | 1.07 | 0.98 | 1.04 |
| Target Coverage | 1.14 | 1.02 | 1.17 |
| Flanked On-target | 1.05 | 0.96 | 1.01 |
| Total DNA Yield | 1.94 | 2.07 | 4.02 |

Ratio: $\frac{\text{Test Condition}}{\text{Standard Condition}}$
Bold font: Superior;
Normal font: Equivalent to xGEN;
Italic font: Inferior.

TABLE 10

Comparison Ratios for Equivalently prepared Prism and Kapa Libraries

| AML | xGEN: Prism/Kapp | Prism/Hyb V2/xGEN | Prism Hyb V2/Kapp xGEN |
|---|---|---|---|
| Probe 70/30 | *1.93* | 0.16 | 0.31 |
| Target 70/30 | *2.16* | 0.13 | 0.28 |
| Uniformity (Fold 80) | *1.24* | 0.65 | 0.81 |
| Sampling Diversity | *0.81* | 1.23 | 0.99 |
| Redundancy | *1.19* | 0.88 | 1.05 |
| Probe Coverage | 0.99 | 1.07 | 1.05 |
| Target Coverage | 1.09 | 1.08 | 1.17 |
| Flanked On-target | 0.99 | 1.06 | 1.05 |
| Total DNA Yield | 2.18 | 1.89 | 4.12 |

Ratio: $\frac{\text{Test Condition}}{\text{Standard Condition}}$
Bold font: Superior;
Normal font: Equivalent to xGEN;
Italic font: Inferior.

TABLE 11

Comparison Ratios for Equivalently prepared Prism and Kapa Libraries

| Standard 500 | xGEN: Prism/Kapp | Prism/Hyb V2/xGEN | Prism Hyb V2/Kapp xGEN |
|---|---|---|---|
| Probe 70/30 | 3.17 | 0.20 | 0.65 |
| Target 70/30 | 5.08 | 0.26 | *1.31* |
| Uniformity (Fold 80) | 1.23 | 0.77 | 0.95 |
| Sampling Diversity | *0.74* | 1.15 | 0.85 |
| Redundancy | *1.50* | 1.36 | 2.04 |
| Probe Coverage | 1.10 | 1.47 | 1.61 |
| Target Coverage | 1.19 | 1.42 | 1.69 |
| Flanked On-target | 1.10 | 1.43 | 1.56 |
| Total DNA Yield | 1.64 | *0.80* | 1.32 |

Ratio: $\frac{\text{Test Condition}}{\text{Standard Condition}}$
Bold font: Superior;
Normal font: Equivalent to xGEN;
Italic font: Inferior.

For the 2-hour hybridization, the Prism library metrics improved using the Hyb V2 workflow. The 2-hour hybridization using Hyb V2-Prism has better overall metrics compared with overnight hybridization using xGEN-Kapa and the coverage is equivalent or better.

In addition, xGEN hyb-capture is GC-biased for all panels tested. The Hyb V2 method mitigates the Prism library GC-bias (e.g., the method rescues AT content). This demonstrates that the Hyb V2 method is tunable at the "Melt" step and can be used to modulate GC-bias.

What is claimed:

1. A method for enriching a population of nucleic acid target sequences in a sample comprising:
    (a) providing a sample of nucleic acid molecules comprising a plurality of target nucleic acid sequences and a plurality of off-target nucleic acid sequences;
    (b) hybridizing the sample to a panel of nucleic acid probes that are complementary to the plurality of target nucleic acid sequences under hybridization conditions to generate a probe/target complex;
    (c) selectively immobilizing the probe/target complex to form an immobilized probe/target complex and adding a melt buffer;
    (d) heating the immobilized probe/target complex and the melt buffer to a temperature at or below the aggregate $T_m$ of the probe/target complex for a period of time sufficient to disassociate the off-target nucleic acid sequences; and
    (e) washing the immobilized probe/target complex to remove non-hybridized nucleic acid sequences and off-target nucleic acid sequences from the hybridized plurality of target nucleic acid sequences, thereby enriching for the plurality of target nucleic acid sequences in the sample;
    wherein step (d) is performed prior to step (e).

2. The method of claim 1, wherein the panel of nucleic acid probes that are complementary to the plurality of target nucleic acid sequences further comprises a capture moiety.

3. The method of claim 2, wherein the capture moiety is biotin.

4. The method of claim 1, wherein the hybridization conditions comprise a hybridization buffer comprising one or more of:
    (a) salts comprising monovalent, divalent, sodium, ammonium, cesium, or manganese, chlorides, citrates, sulfates, perchlorates, isothiocyanates, or guanidinium;
    (b) chelating agents comprising one or more of ethylenediaminetetraacetic acid (EDTA), ethylene glycol-bis(β-aminoethyl ether)-N,N,N',N'-tetraacetic acid (EGTA), or (1,2-bis(o-aminophenoxy)ethane-N,N,N',N'-tetraacetic acid (BAPTA);
    (c) buffering agents comprising one or more of tris (hydroxymethyl)aminomethane (Tris); 2-(bis(2-hydroxyethyl)amino)acetic acid) (Bicine); (N-[tris(hydroxymethyl)methyl]glycine (Tricine); [tris (hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl] amino]ethanesulfonic acid (TES); 3-(N-morpholino) propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate);
    (d) detergents comprising one or more of sodium dodecylsulfate (SDS), polysorbate 20, octyl phenol ethoxylate, octylphenoxypolyethoxyethanol, nonyl phenoxypolyethoxylethanol (NP-40), or cetrimonium bromide (CTAB); or
- (e) additives comprising one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

5. The method of claim 4, wherein the hybridization buffer contains formamide.

6. The method of claim 4, wherein the hybridization buffer does not contain formamide.

7. The method of claim 1, wherein the hybridization conditions comprise an incubation time ranging from about 10 minutes to about 48 hours.

8. The method of claim 1, wherein the hybridization conditions comprise an incubation time ranging from about 2 hours to overnight.

9. The method of claim 1, wherein the hybridization conditions comprise an incubation temperature ranging from about 55° C. to about 75° C.

10. The method of claim 1, wherein the hybridization conditions comprise an incubation temperature ranging from about 60° C. to about 70° C.

11. The method of claim 1, wherein the hybridization conditions comprise an incubation time of about 2 hours and an incubation temperature of about 65° C.

12. The method of claim 1, wherein the probe/target complex is selectively immobilized using streptavidin beads.

13. The method of claim 1, wherein the probe/target complex is selectively immobilized under conditions comprising an incubation time ranging from about 10 minutes to about 48 hours.

14. The method of claim 1, wherein the probe/target complex is selectively immobilized under conditions comprising an incubation temperature ranging from about 20° C. to about 40° C.

15. The method of claim 1, wherein the probe/target complex is selectively immobilized under conditions comprising an incubation time of about 30 minutes and an incubation temperature of room temperature.

16. The method of claim 1, wherein the melt buffer comprises one or more of:
- (a) salts comprising one or more of monovalent, divalent, sodium, ammonium, cesium, or manganese, chlorides, citrates, sulfates, perchlorates, isothiocyanates, or guanidinium;
- (b) chelating agents comprising one or more of ethylenediaminetetraacetic acid (EDTA), ethylene glycol-bis(β-aminoethyl ether)-N,N,N',N'-tetraacetic acid (EGTA), or (1,2-bis(o-aminophenoxy)ethane-N,N,N',N'-tetraacetic acid (BAPTA);
- (c) buffering agents comprising one or more of tris (hydroxymethyl)aminomethane (Tris); 2-(bis(2-hydroxyethyl)amino)acetic acid) (Bicine); (N-[tris(hydroxymethyl)methyl]glycine (Tricine); [tris (hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl] amino]ethanesulfonic acid (TES); 3-(N-morpholino) propanesulfonic acid (MOPS); piperazine-N,N'-bis(2-ethanesulfonic acid) (PIPES); 2-(N-morpholino)ethanesulfonic acid (MES); or dimethylarsenic acid (Cacodylate);
- (d) detergents comprising one or more of sodium dodecylsulfate (SDS), polysorbate 20, octyl phenol ethoxylate, octylphenoxypolyethoxyethanol, nonyl phenoxypolyethoxylethanol (NP-40), or cetrimonium bromide (CTAB); or
- (e) additives comprising one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

17. The method of claim 1, wherein the heating of the immobilized probe/target complex comprises an incubation time ranging from about 5 minutes to about 1 hour.

18. The method of claim 1, wherein the heating of the immobilized probe/target complex comprises an incubation temperature ranging from about 50° C. to about 70° C.

19. The method of claim 1, wherein the heating of the immobilized probe/target complex comprises an incubation time of about 20 minutes and an incubation temperature of about 55° C.

20. The method of claim 1, wherein the washing of the immobilized probe/target complex comprises two distinct wash buffers, wherein each wash buffer independently comprises one or more of:
- (a) salts comprising one or more of monovalent, divalent, sodium, ammonium, cesium, or manganese, chlorides, citrates, sulfates, perchlorates, isothiocyanates, or guanidinium;
- (b) chelating agents comprising one or more of ethylenediaminetetraacetic acid (EDTA), ethylene glycol-bis(β-aminoethyl ether)-N,N,N',N'-tetraacetic acid (EGTA), or (1,2-bis(o-aminophenoxy)ethane-N,N,N',N'-tetraacetic acid (BAPTA);
- (c) buffering agents comprising one or more of tris (hydroxymethyl)aminomethane (Tris); 2-(bis(2-hydroxyethyl)amino)acetic acid) (Bicine); (N-[tris(hydroxymethyl)methyl]glycine (Tricine); [tris (hydroxymethyl)methylamino] propanesulfonic acid (TAPS); 3-[N-tris(hydroxymethyl)methylamino]-2-hydroxypropanesulfonic acid (TAPSO); 4-(2-hydroxyethyl)-1-piperazineethanesulfonic acid (HEPES); 2-[[1,3-dihydroxy-2-(hydroxymethyl)propan-2-yl] amino]ethanesulfonic acid (TES); 3-(N-morpholino) propanesulfonic acid (MOPS); piperazine-N,N'-bis(2-ethanesulfonic acid) (PIPES); 2-(N-morpholino) ethanesulfonic acid (MES); or dimethylarsenic acid (Cacodylate);
- (d) detergents comprising one or more of sodium dodecylsulfate (SDS), polysorbate 20, octyl phenol ethoxylate, octylphenoxypolyethoxyethanol, nonyl phenoxypolyethoxylethanol (NP-40), or cetrimonium bromide (CTAB); or
- (e) additives comprising one or more of glycine, betaine, glycine-betaine, 7-deaza-2'-deoxyguanosine, dimethyl sulfoxide (DMSO), polyethylene glycols 400-1,000,000, glycerol, magnesium, tetramethyl ammonium chloride (TMAC), tetraethylammonium chloride (TEAC), triethylamine hydrochloride, ethylene carbonate, dextran sulfate, or bovine serum albumin (BSA).

21. The method of claim 1, wherein the washing of the immobilized probe/target complex comprises an incubation time of about 5 minutes to about 15 minutes and an incubation temperature of about 60° C.

* * * * *